(12) United States Patent
Chen et al.

(10) Patent No.: US 12,303,295 B2
(45) Date of Patent: May 20, 2025

(54) SIGNAL ADJUSTMENT METHOD FOR PPG APPARATUS AND PPG APPARATUS

(71) Applicant: SHENZHEN GOODIX TECHNOLOGY CO., LTD., Shenzhen (CN)

(72) Inventors: Liangshou Chen, Shenzhen (CN); Saiwen Lu, Shenzhen (CN)

(73) Assignee: SHENZHEN GOODIX TECHNOLOGY CO., LTD., Guangdong (CN)

(*) Notice: Subject to any disclaimer, the term of this patent is extended or adjusted under 35 U.S.C. 154(b) by 720 days.

(21) Appl. No.: 17/709,857

(22) Filed: Mar. 31, 2022

(65) Prior Publication Data

US 2022/0218288 A1 Jul. 14, 2022

Related U.S. Application Data

(63) Continuation of application No. PCT/CN2020/100694, filed on Jul. 7, 2020.

(51) Int. Cl.
*A61B 5/00* (2006.01)
*A61B 5/024* (2006.01)

(52) U.S. Cl.
CPC ........ *A61B 5/7225* (2013.01); *A61B 5/02416* (2013.01); *A61B 5/7221* (2013.01); *A61B 2560/0242* (2013.01)

(58) Field of Classification Search
CPC ........ A61B 2560/0242; A61B 5/02416; A61B 5/7221; A61B 5/7225
See application file for complete search history.

(56) References Cited

U.S. PATENT DOCUMENTS

2003/0060693 A1 3/2003 Monfre et al.
2006/0089557 A1 4/2006 Grajales et al.
(Continued)

FOREIGN PATENT DOCUMENTS

CN 1929777 A 3/2007
CN 1933773 A 3/2007
(Continued)

OTHER PUBLICATIONS

Extended Search Report in European Application No. 20944067.6 dated Jul. 7, 2022, 9 pages.
(Continued)

*Primary Examiner* — Mark D Remaly
(74) *Attorney, Agent, or Firm* — Suiter Swantz IP

(57) ABSTRACT

Provided are a signal adjustment method for a PPG apparatus and a PPG apparatus. The method comprises: when background light data or actual effective light data does not meet a preset background light data range or a preset first effective light data range, performing a dimming operation comprising: determining an estimated current transfer ratio; estimating a driving current required by a light source and a gain required by an analog front end; calculating estimated effective light data of a PPG apparatus according to the estimated driving current required by the light source, the gain required by the analog front end, and the estimated current transfer ratio; when the estimated effective light data meets a preset second effective light data range, generating a to-be-adjusted current/gain value according to the estimated driving current required by the light source and the gain required by the analog front end.

20 Claims, 7 Drawing Sheets

(56) References Cited

U.S. PATENT DOCUMENTS

2018/0078151 A1    3/2018   Allec et al.
2020/0138379 A1    5/2020   Huiku et al.

FOREIGN PATENT DOCUMENTS

| | | | |
|---|---|---|---|
| CN | 101677773 | A | 3/2010 |
| CN | 103957793 | A | 7/2014 |
| CN | 103209641 | B | 4/2015 |
| CN | 108652605 | A | 10/2018 |
| CN | 109863703 | A | 6/2019 |
| CN | 110604559 | A | 12/2019 |
| CN | 111202529 | A | 5/2020 |
| EP | 3434182 | A1 | 1/2019 |

OTHER PUBLICATIONS

International Search Report in Application No. PCT/US2020/100694, dated Mar. 26, 2021, 6 pages (With English Translation).
Office Action in Chinese Application No. 202010647476.X dated Aug. 25, 2020, 10 pages (With English Translation).

SIGNAL ADJUSTMENT METHOD FOR PPG APPARATUS AND PPG APPARATUS

PRIORITY

The present application constitutes a bypass continuation of International Application PCT/CN2020/100694, filed on Jul. 7, 2020, which is incorporated herein by reference in the entirety.

TECHNICAL FIELD

The present disclosure relates to the technical field of intelligent apparatus, and in particular, to a signal adjustment method for a PPG apparatus and a PPG apparatus.

BACKGROUND

A heart rate can reflect a person's heart activity ability and further the person's health status. Electrocardiograms are mostly used to measure heart rates in hospitals. Such measurement is inconvenient in daily activities and sports.

A PPG (photoplethysmographic) scheme is a method in which a controllable light source, such as a light emitting diode (LED), is used to illuminate human skins, and an analog front end (AFE) is used to connect a photodiode (PD) as a detector to measure attenuated light obtained after light emitted by the light source is reflected and absorbed by human blood vessels and tissue, so as to trace a pulsatile status of the blood vessels and measure a pulse wave. Due to the advantages of simply obtaining measurement signals and easily wearing a measurement apparatus, the PPG scheme has gradually become a main method for measuring blood oxygen, pulse, and heart rates under non-hospital conditions.

In a PPG apparatus, after a detector samples a PPG signal, the analog PPG signal is transmitted to an analog-to-digital converter (ADC) to be converted into a digital PPG signal. The ADC outputs the digital PPG signal to other control logics, such as heart rate and heart rate variability (HRV) algorithms. The heart rate and HRV algorithms have high requirements on stability of the PPG signal. When an alternating current/direct current (AC/DC) ratio of the PPG signal is constant, the AC increases as the DC increases such that accuracy of the heart rate and HRV algorithms is improved. A dynamic range of the ADC is limited to some extent, therefore, to make the stability quality of the PPG signal be optimal, the PPG signal needs to be converged within a dynamic range of the ADC.

In actual application scenarios, changes in component parameters of the PPG apparatus (for example, changes in component parameters caused by hardware performance degradation of components of the PPG apparatus) and changes in a use environment directly affect sampling of the PPG signal. For example, the PPG signal is affected by background light, an intensity and angle of light emitted by a light source of the PPG apparatus, discreteness of the light source of the PPG apparatus, a distance and angle of a data sampling window from the skin, a color of the skin, characteristics of subcutaneous tissue, a size of a PD, optical-to-electrical conversion efficiency, a gain of an AFE, and the like. When the component parameters of the PPG apparatus and/or the use environment change, the PPG signal may go beyond the dynamic range of the ADC.

SUMMARY

In view of the problem that a PPG signal of a PPG apparatus is beyond a dynamic range of an ADC, the present disclosure provides a signal adjustment method for a PPG apparatus, a PPG apparatus, and a computer-readable storage medium.

Embodiments of the present disclosure adopt the following technical solutions.

In a first aspect of embodiments of the present disclosure, a signal adjustment method for a pshotoplethysmographic (PPG) apparatus is provided, and the method includes: sampling background light data and mixed light data; determining whether the background light data falls within a preset background light data range, and/or determining whether calculated actual effective light data falls within a preset first effective light data range, where the actual effective light data is a difference between the mixed light data and the background light data; and in response to the background light data being beyond the preset background light data range, or the actual effective light data being beyond the preset first effective light data range, performing a light adjustment operation. The light adjustment operation includes: determining an estimated current transfer ratio (CTR) based on a preset CTR or an actual CTR of the PPG apparatus; estimating a drive current required by a light source of the PPG apparatus and a gain required by an analog front end (AFE) based on a drive current of the light source, a gain of the AFE, and the sampled background light data and mixed light data; calculating estimated effective light data of the PPG apparatus based on the estimated drive current required by the light source, the estimated gain required by the AFE, and the estimated CTR; and determining whether the estimated effective light data falls within a preset second effective light data range; and in response to the estimated effective light data falling within the preset second effective light data range, generating a to-be-adjusted current/gain value based on the estimated drive current required by the light source and gain required by the AFE, so as to adjust the drive current of the light source of the PPG apparatus and the gain of the AFE.

In addition, combined with the first aspect, in an embodiment of the first aspect, the method further includes: in response to the estimated effective light data being beyond the preset second effective light data range, re-estimating, through convergence, the drive current required by the light source and the gain required by the AFE based on the currently estimated drive current required by the light source and gain required by the AFE, so as to recalculate the estimated effective light data; and in response to the recalculated estimated effective light data falling within the preset second effective light data range, generating a to-be-adjusted current/gain value based on the re-estimated drive current required by the light source and gain required by the AFE.

In addition, combined with the first aspect, in an embodiment of the first aspect, the method further includes: in response to the recalculated estimated effective light data being beyond the preset second effective light data range, and the currently estimated drive current and gain falling within a preset adjustable current range and adjustable gain range of the PPG apparatus respectively, re-estimating, through convergence, the drive current required by the light source and the gain required by the AFE.

In addition, combined with the first aspect, in an embodiment of the first aspect, the method further includes: in response to the recalculated estimated effective light data being beyond the preset second effective light data range, and the currently estimated drive current and gain being beyond a preset adjustable current range and adjustable gain range respectively, ending the light adjustment operation.

In addition, combined with the first aspect, in an embodiment of the first aspect, the light adjustment operation further includes: before the drive current required by the light source and the gain required by the AFE are estimated, triggering initial adjustment in response to the background light data being beyond the preset background light data range, where the initial adjustment includes: adjusting, through convergence, the gain of the AFE.

In addition, combined with the first aspect, in an embodiment of the first aspect, said adjusting, through convergence, the gain of the AFE includes: in response to the background light data being greater than an upper limit of the preset background light data range, reducing the gain of the AFE; and in response to the background light data being less than a lower limit of the preset background light data range, increasing the gain of the AFE.

In addition, combined with the first aspect, in an embodiment of the first aspect, the drive current required by the light source and the gain required by the AFE are estimated through dichotomization or stepping.

In addition, combined with the first aspect, in an embodiment of the first aspect, the method further includes: during the drive current required by the light source and the gain required by the AFE being estimated, in response to the drive current of the light source falling within the preset adjustable current range of the PPG apparatus, adjusting the drive current of the light source; and in response to the drive current of the light source being beyond the preset adjustable current range of the PPG apparatus, and the gain of the AFE falling within the preset adjustable gain range of the PPG apparatus, adjusting the gain of the AFE.

In addition, combined with the first aspect, in an embodiment of the first aspect, said determining an estimated CTR based on an actual CTR of a PPG apparatus includes: calculating the actual CTR when the PPG apparatus samples the mixed light data based on a drive current of the light source and a gain of the AFE when the mixed light data is sampled, and the calculated actual effective light data, where the estimated CTR is an actual CTR when the mixed light data is sampled for one time, or an average value of a plurality of actual CTRs when the mixed light data is sampled for a plurality of times.

In addition, combined with the first aspect, in an embodiment of the first aspect, said determining whether the background light data falls within a preset background light data range includes: in response to background light data sampled for an $n^{th}$ time or for each time of n consecutive times being beyond the preset background light data range, determining that the background light data is beyond the preset background light data range.

In addition, combined with the first aspect, in an embodiment of the first aspect, said determining whether calculated actual effective light data falls within a preset first effective light data range includes: in response to effective light data calculated for an $n^{th}$ time or for each time of n consecutive times being beyond the preset first effective light data range, determining that the effective light data is beyond the preset first effective light data range.

In addition, combined with the first aspect, in an embodiment of the first aspect, the method further includes: in response to a light leakage level threshold falling within the preset first effective light data range, defining that a lower limit of the second effective light data range is the light leakage level threshold, where the light leakage level threshold is a parameter value determined based on a light leakage status of the PPG apparatus in an application scenario.

In addition, combined with the first aspect, in an embodiment of the first aspect, said generating a to-be-adjusted current/gain value based on the estimated drive current required by the light source and gain required by the AFE in response to the estimated effective light data falling within the preset second effective light data range includes: obtaining an apparatus jitter parameter of the PPG apparatus; calling or calculating a corresponding attenuation coefficient based on the apparatus jitter parameter; and performing attenuation calculation on the estimated drive current required by the light source and gain required by the AFE based on the attenuation coefficient, and using a result of the attenuation calculation as the to-be-adjusted current/gain value.

In addition, combined with the first aspect, in an embodiment of the first aspect, the method further includes: performing sampling verification, where the sampling verification includes: after the drive current of the light source of the PPG apparatus and the gain of the AFE are adjusted based on the to-be-adjusted current/gain value, obtaining background light data and mixed light data; and recalculating the actual effective light data based on the obtained background light data and mixed light data; and in response to the recalculated actual effective light data being beyond the second effective light data range, cyclically performing the light adjustment operation and the sampling verification.

In a second aspect of embodiments of the present disclosure, a PPG apparatus is provided, and the PPG apparatus includes a memory configured to store a computer program instruction and a processor configured to execute the computer program instruction. When the computer program instruction is executed by the processor, the PPG apparatus is triggered to perform steps of the method according to the first aspect.

In a third aspect of embodiments of the present disclosure, a computer-readable storage medium is provided. The computer-readable storage medium stores a computer program, and when the computer program runs on a PPG apparatus, the PPG apparatus performs steps of the method according to the first aspect.

At least one of the foregoing technical solutions adopted in the embodiments of the present disclosure can achieve the following beneficial effects.

According to the method in the embodiments of the present disclosure, the to-be-adjusted current/gain value can be obtained, and the drive current of the light source of the PPG apparatus and the gain of the AFE can be adjusted based on the to-be-adjusted current/gain value such that the PPG signal of the PPG apparatus can be converged within the dynamic range of the ADC. In comparison with the prior art, in the method in the embodiments of the present disclosure, the number of times the drive current of the light source of the PPG apparatus and the gain of the AFE are actually adjusted can be greatly decreased, thereby effectively reducing the time taken to perform the light adjustment operation, and thus improving a convergence speed of the PPG signal and work efficiency and adaptivity of the PPG apparatus.

DETAILED DESCRIPTION

Figure 1:
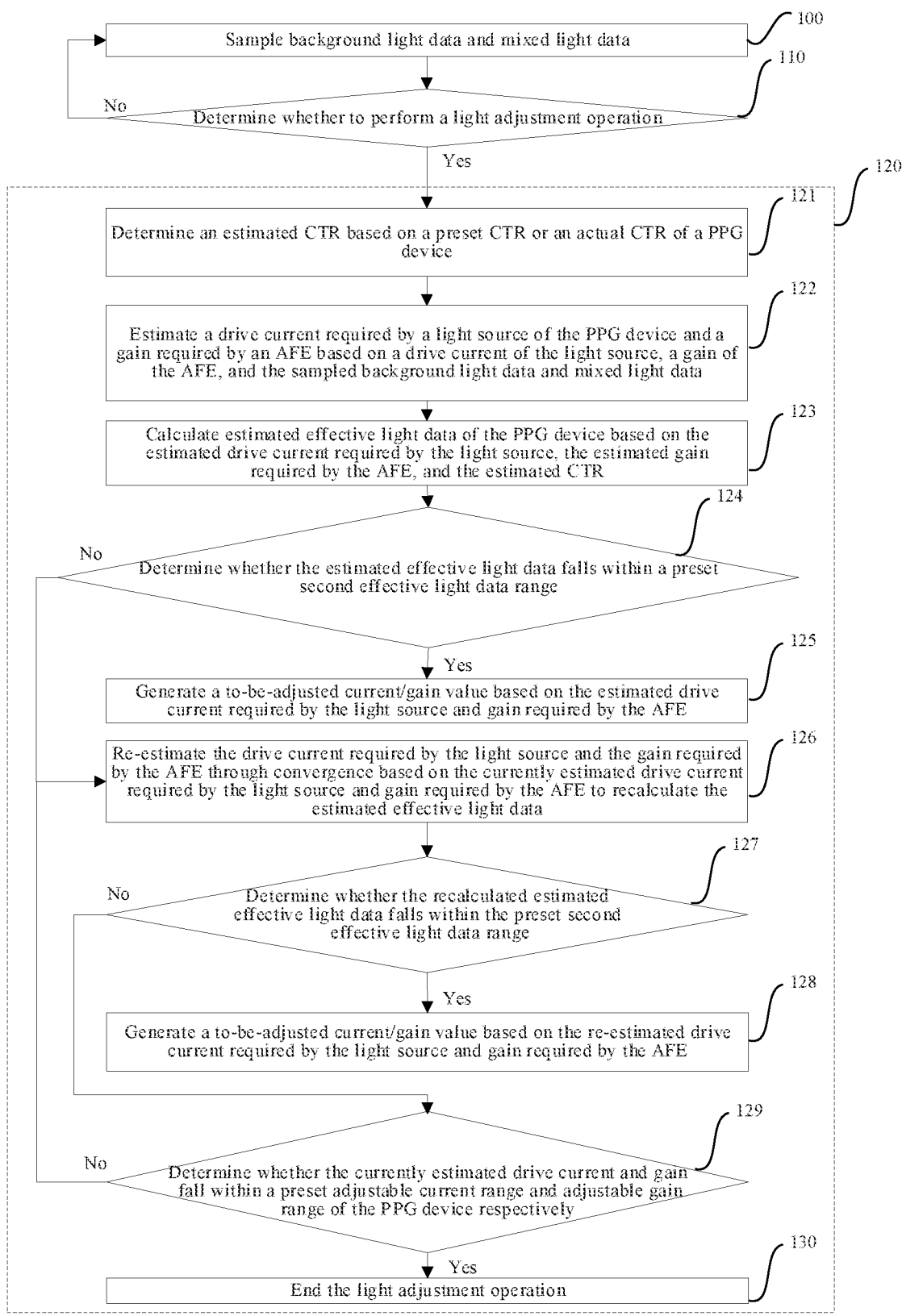
FIG. 1 is a flowchart of an embodiment of a signal adjustment method for a PPG apparatus according to the present disclosure.

To make the objective, technical solutions, and advantages of the present disclosure clearer, the technical solutions in the present disclosure are described in detail below with reference to embodiments and accompanying drawings of the present disclosure. Apparently, the described embodiments are some rather than all of the embodiments of the present disclosure. All other embodiments obtained by those of ordinary skill in the art based on the embodiments of the present disclosure without creative efforts shall fall within a protection scope of the present disclosure.

The terms used in the embodiments of the present disclosure are used only to explain the embodiments of the present disclosure, and are not intended to limit the present disclosure.

In view of the problem that a PPG signal of a PPG apparatus is beyond a dynamic range of an ADC, an embodiment of the present disclosure provides a signal adjustment method for a PPG apparatus. Specifically, in an embodiment of the present disclosure, a light adjustment operation is triggered when the PPG signal is beyond the dynamic range of the ADC, and a to-be-adjusted current/gain value is generated during the light adjustment operation to adjust a drive current of a light source of the PPG apparatus and a gain of an AFE. The PPG apparatus adjusts the drive current of the light source and/or the gain of the AFE based on the generated to-be-adjusted current/gain value such that the PPG signal is converged within the dynamic range of the ADC as soon as possible. For example, if a PPG signal sampled by the ADC is lower than a lower limit of the dynamic range of the ADC, the drive current of the light source and/or the gain of the AFE need to be increased. If the PPG signal sampled by the ADC is higher than an upper limit of the dynamic range of the ADC, the drive current of the light source and/or the gain of the AFE need to be decreased.

Further, based on a working mode of the PPG apparatus, the PPG signal is light data sampled by the PPG apparatus through a detector. Therefore, a light data range may be preset based on the dynamic range of the ADC, and the light adjustment operation is triggered if the light data sampled by the PPG apparatus is beyond the preset light data range.

Further, a PPG scheme is a method that samples attenuated light obtained after light emitted by a light source of an apparatus is reflected and absorbed by human blood vessels and tissue to trace a pulsatile status of the blood vessels and measure a pulse wave. Therefore, when the light source of the PPG apparatus is turned on, the light data sampled by the PPG apparatus includes light data obtained after the PPG apparatus samples attenuated light obtained after light emitted by the PPG apparatus is reflected and absorbed by human blood vessels and tissue. The light data obtained after the PPG apparatus samples the attenuated light obtained after the light emitted by the PPG apparatus is reflected and absorbed by the human blood vessels and tissue is defined as effective light data. The effective light data is denoted as RawdataReal.

Further, in an actual application scenario of the PPG apparatus, there is not only the light source of the PPG apparatus, but also a light source other than the light source of the PPG apparatus, such as sunlight or lamplight. When the light source of the PPG apparatus is turned off, the light data sampled by the PPG apparatus is light data from the light source other than the light source of the PPG apparatus. The light data from the light source other than the light source of the PPG apparatus and sampled by the PPG apparatus is defined as background light data. The background light data is denoted as RawdataBg.

Because the detector of the PPG apparatus cannot prevent sampling of the light data from the light source other than the light source of the PPG apparatus, when the light source of the PPG apparatus is turned on, the light data sampled by the PPG apparatus is mixed light data that includes both the effective light data and background light data. When the light source of the PPG apparatus is turned on, the mixed light data sampled by the PPG apparatus is denoted as RawdataMix.

$$RawdataReal = RawdataMix - RawdataBg \quad (1).$$

Therefore, in an embodiment of the present disclosure, a background light data range and/or an effective light data range are preset based on the dynamic range of the ADC. It is determined whether the background light data sampled by the PPG apparatus falls within the preset background light data range, and/or the effective light data sampled by the PPG apparatus falls within the preset effective light data range, to determine whether the light adjustment operation needs to be triggered.

Further, in practical application scenarios, there are many implementations of the light adjustment operation of the PPG apparatus. A feasible light adjustment operation scheme is to increase or decrease the drive current of the light source in fixed steps and/or increase or decrease the gain of the AFE in fixed steps in each light adjustment operation, and the effective light data is measured after each light adjustment operation. Through a plurality of adjustments, the measured effective light data finally falls within the preset effective light range. Because the light adjustment operation needs to be repeated a plurality of times in the foregoing adjustment scheme, a data processing amount is greatly increased, and time taken to perform the light adjustment operation is increased. This reduces response sensitivity of the light adjustment operation of the PPG apparatus.

In view of the problem of the foregoing light adjustment operation scheme, in an embodiment of the present disclosure, an adjustment mode estimated based on the effective light data is used during the light adjustment operation. Specifically, during the light adjustment operation, before the drive current of the light source and/or the gain of the AFE are adjusted, a drive current required by the light source of the PPG apparatus and a gain required by the AFE are first estimated, and then the drive current of the light source and/or the gain of the AFE are adjusted based on the estimated drive current required by the light source of the PPG apparatus and gain required by the AFE. In the foregoing process, effective light data ('RawdataReal) estimated based on the estimated drive current required by the light source of the PPG apparatus and gain required by the AFE falls within the preset effective light data range. Because 'RawdataReal is highly consistent with RawdataReal obtained after the light adjustment operation is performed, a number of repetitions of the light adjustment operation is greatly reduced.

Specifically, in the embodiments of the present disclosure, the effective light data is estimated based on a CTR of the PPG apparatus. The CTR, the drive current (current) of the light source of the PPG apparatus, the gain (gain) of the AFE, and the effective light data (RawdataReal) sampled by the PPG apparatus satisfy the following formula:

$$CTR \times current \times gain = RawdataReal \quad (2).$$

The technical solutions provided in the embodiments of the present disclosure are described in detail below with reference to the accompanying drawings.

FIG. 1 is a flowchart of an embodiment of a signal adjustment method for a PPG apparatus according to the present disclosure. In an embodiment of the present disclosure, as shown in FIG. 1, the method includes the following steps.

Step 100: background light data and mixed light data are sampled. For example, measured background light data sampled by a PPG apparatus for an $n^{th}$ time and mixed light data sampled for the $n^{th}$ time (n is a natural number greater than zero) are obtained.

Step 110: it is determined whether to perform a light adjustment operation, including the following steps.

It is determined whether the background light data falls within a preset background light data range, and/or it is determined whether calculated actual effective light data falls within a preset first effective light data range, where the actual effective light data is a difference between the mixed light data and the background light data.

Then, the light adjustment operation is performed if the background light data is beyond the preset background light data range, or the actual effective light data is beyond the preset first effective light data range.

Then, if the light adjustment operation is not triggered, step 100 is performed.

If the light adjustment operation is triggered, step 120 is performed.

Step 120: the light adjustment operation is performed. The light adjustment operation includes the following steps.

Step 121: an estimated CTR is determined based on a preset CTR or an actual CTR of the PPG apparatus.

Step 122: a drive current required by a light source of the PPG apparatus and a gain required by an AFE is estimated based on a drive current of the light source, a gain of the AFE, and the sampled background light data and mixed light data.

Step 123: estimated effective light data of the PPG apparatus is calculated based on the estimated drive current required by the light source, the estimated gain required by the AFE, and the estimated CTR.

Step 124: it is determined whether the estimated effective light data falls within a preset second effective light data range.

If the estimated effective light data falls within the preset second effective light data range, step 125 is performed.

Step 125: a to-be-adjusted current/gain value is generated based on the estimated drive current required by the light source and gain required by the AFE, so as to adjust the drive current of the light source of the PPG apparatus and the gain of the AFE.

In a specific application scenario, the preset background light data range, first effective light data range, and second effective light data range in the foregoing process are numerical ranges determined by a background light data status and an effective light data status corresponding to a PPG signal within a dynamic range of an ADC. In other words, if the background light data is beyond the background light data range or the effective light data is beyond the first effective light data range, the PPG signal is beyond the dynamic range of the ADC. If the effective light data falls within the second effective light data range, the PPG signal is converged within the dynamic range of the ADC.

In the method of an embodiment shown in FIG. 1, when the PPG signal is beyond the dynamic range of the ADC, the to-be-adjusted current/gain value for adjusting the drive current of the light source of the PPG apparatus and the gain of the AFE can be obtained such that the PPG signal of the PPG apparatus under various usage conditions can be converged within the dynamic range of the ADC to ensure quality of the PPG signal and improve adaptivity of the PPG apparatus.

In comparison with the prior art, in the method of the embodiment shown in FIG. 1, time to trigger the light adjustment operation is determined by monitoring the background light data and/or effective light data, and the to-be-adjusted current/gain value is generated only when the estimated effective light data falls within the dynamic range of the ADC for adjusting the drive current of the light source of the PPG apparatus and the gain of the AFE, to ensure response sensitivity of the light adjustment operation and adaptivity of the PPG apparatus, and also effectively prevent unnecessary light adjustment operations (for example, adjusting the drive current of the light source of the PPG apparatus and the gain of the AFE for a plurality of times, sampling the PPG signal after the light adjustment for a plurality of times, and performing data processing on the PPG signal after the light adjustment for a plurality of times). This greatly reduces a frequency of the light adjustment operation, reduces data processing pressure and power consumption of the PPG apparatus, ensures work efficiency and a convergence speed of the PPG apparatus, and prolongs a service life of the PPG apparatus.

Further, in the method of the embodiment shown in FIG. 1, during the light adjustment operation, the drive current required by the light source and the gain required by the AFE are estimated, and the estimated effective light data is calculated based on the CTR, to determine whether the estimated drive current and gain can make the effective light data fall within the preset effective light data range, and finally obtain the drive current required by the light source and the gain required by the AFE that can make the estimated effective light data fall within the preset effective light data range.

Because the estimated effective light data is highly consistent with the calculated actual effective light data sampled by the PPG apparatus, after the drive current of the light source and the gain of the AFE are adjusted based on the estimated drive current required by the light source and gain required by the AFE, the calculated actual effective light data sampled by the PPG apparatus can fall within the preset second effective light data range. In other words, the PPG signal can be converged within the dynamic range of the ADC.

The process of obtaining the drive current required by the light source and the gain required by the AFE that can make the estimated effective light data fall within the preset effective light data range does not require actual adjustment of the drive current of the light source and the gain of the AFE. Therefore, in comparison with the prior art, in the method of the embodiment shown in FIG. 1, the number of times the drive current of the light source of the PPG apparatus and the gain of the AFE are actually adjusted can be greatly decreased, to effectively reduce the time taken to perform the light adjustment operation, and improve a convergence speed of the PPG signal and the work efficiency of the PPG apparatus.

Further, in an embodiment of the present disclosure, after step 124, if the estimated effective light data is beyond the preset second effective light data range, the drive current required by the light source and the gain required by the AFE are re-estimated through convergence based on the currently estimated drive current required by the light source and gain required by the AFE, to recalculate the estimated effective light data.

If the recalculated estimated effective light data falls within the preset second effective light data range, a to-be-adjusted current/gain value is generated based on the re-estimated drive current required by the light source and gain required by the AFE.

The re-estimation can ensure that the finally generated to-be-adjusted current/gain value meets a requirement of the dynamic range of the ADC. Because the re-estimation is still a calculation process and does not include an actual PPG adjustment process, the re-estimation does not cause significant time consumption. The re-estimation can greatly reduce the number of times the drive current of the light source of the PPG apparatus and the gain of the AFE are actually adjusted, thereby effectively reducing the time taken to perform the light adjustment operation, and improving the convergence speed of the PPG signal and the work efficiency of the PPG apparatus.

Specifically, an embodiment of the present disclosure is as shown in FIG. 1.

If the estimated effective light data is beyond the preset second effective light data range, step 126 is performed.

Step 126: the drive current required by the light source and the gain required by the AFE are re-estimated through convergence based on the currently estimated drive current required by the light source and gain required by the AFE, to recalculate the estimated effective light data.

Step 127: it is determined whether the recalculated estimated effective light data falls within the preset second effective light data range.

If the recalculated estimated effective light data falls within the preset second effective light data range, step 128 is performed.

Step 128: a to-be-adjusted current/gain value is generated based on the re-estimated drive current required by the light source and gain required by the AFE.

Further, in actual application scenarios, due to limitations of hardware conditions and other factors, the drive current of the light source of the PPG apparatus and the gain of the AFE have an adjustable range. The PPG apparatus can work normally only when the drive current of the light source of the PPG apparatus and the gain of the AFE fall within their respective adjustable ranges. When the drive current of the light source of the PPG apparatus or the gain of the AFE is set beyond the adjustable range, the PPG apparatus cannot work normally.

For example, an LED of the PPG apparatus has a maximum operating current D2 and a minimum operating current D1. In other words, an adjustable range of a drive current of the LED is [D1, D2] (for example, [D1, D2] is [0, 100] with a unit of mA in an application scenario). In this case, when the drive current of the LED is greater than D2, the LED may be burned, and when the drive current of the LED is less than D1, the LED cannot emit light.

In another example, the gain of the AFE of the PPG apparatus has a maximum gain G2 and a minimum gain G1. In other words, the adjustable range of the gain of the AFE is [G1, G2] (for example, [G1, G2] is 1100, 10001 in an application scenario). In this case, when the gain of the AFE is to be set to a value greater than G2 or less than G1, the setting may fail or the PPG apparatus cannot work under the setting.

Therefore, in the process of estimating and re-estimating the drive current required by the light source and the gain required by the AFE, it needs to ensure that the estimated drive current required by the light source and the gain required by the AFE fall within the adjustable ranges of the drive current of the light source and the gain of the AFE respectively. For example, in an application scenario, the drive current of the LED or the gain of the AFE needs to be increased, and if the drive current of the LED and the gain of the AFE each reach an upper limit, it indicates that neither the drive current of the LED nor the gain of the AFE has room for adjustment, working parameters cannot be adjusted, and the adjustment fails.

Specifically, in an embodiment of the present disclosure, after step 127, if the recalculated estimated effective light data is beyond the preset second effective light data range, and the currently estimated drive current and gain fall within a preset adjustable current range and adjustable gain range of the PPG apparatus respectively, the drive current required by the light source and the gain required by the AFE are re-estimated through convergence.

Specifically, an embodiment of the present disclosure is as shown in FIG. 1.

If the recalculated estimated effective light data is beyond the preset second effective light data range, step 129 is performed.

Step 129: it is determined whether the currently estimated drive current and gain fall within the preset adjustable current range and adjustable gain range of the PPG apparatus respectively.

If the currently estimated drive current and gain fall within the preset adjustable current range and adjustable gain range of the PPG apparatus respectively, step 126 is performed.

Further, in an embodiment of the present disclosure, after step 127, if the recalculated estimated effective light data is beyond the preset second effective light data range, and the currently estimated drive current and gain are beyond the preset adjustable current range and adjustable gain range respectively, the light adjustment operation stops.

Specifically, in an embodiment of the present disclosure, as shown in FIG. 1, after step 129:

if the currently estimated drive current and gain are beyond the preset adjustable current range and adjustable gain range of the PPG apparatus respectively, step 130 is performed.

Step 130: the light adjustment operation stops.

Adding the step of determining of the adjustable current range and the adjustable gain range can effectively prevent the finally generated to-be-adjusted current/gain value from being beyond the adjustable current range and adjustable gain range, thereby ensuring that the PPG apparatus always works normally, and thus maintaining operation security and stability of the PPG apparatus.

Further, in an embodiment of the present disclosure, in step 130, a light adjustment operation prompt is further output to a user, and/or a light adjustment operation failure flag bit is output such that other components of the PPG apparatus can perform other control processing based on the light adjustment operation failure flag bit (for example, main control outputs another control command based on the flag bit) or an external apparatus can read relevant information about the failure of the light adjustment operation.

Further, in actual application scenarios, each step in the embodiment shown in FIG. 1 may have various implementations. A technical person can implement the steps of the method in the embodiment shown in FIG. 1 by using an appropriate implementation based on specific application scenario requirements. The following examples describe implementations of each step in the embodiment shown in FIG. 1.

Specifically, in an implementation of step 110, if background light data sampled for the $n^{th}$ time or for each time of n consecutive times is beyond the preset background light data range, it is determined that the background light data is beyond the preset background light data range.

In an implementation of step 110, if effective light data calculated for the $n^{th}$ time or for each of n consecutive times is beyond the preset first effective light data range, it is determined that the effective light data is beyond the preset first effective light data range.

For example, in an implementation of step 110:
if the background light data sampled for the $n^{th}$ time is greater than an upper limit of the preset background light data range or less than a lower limit of the preset background light data range, or if the actual effective light data calculated based on the background light data and mixed light data sampled for the $n^{th}$ time is greater than an upper limit of the preset first effective light range or less than a lower limit of the preset first effective light range, it is determined that the light adjustment operation is triggered (to perform step 120).

For example, in an implementation of step 110:
if the background light data sampled for each time of n consecutive times is greater than the upper limit of the preset background light data range or less than the lower limit of the preset background light data range, or if n pieces of actual effective light data calculated based on the background light data and mixed light data sampled for n consecutive times are each greater than the upper limit of the preset first effective light range or less than the lower limit of the preset first effective light range, it is determined that the light adjustment operation is triggered (to perform step 120).

Determining whether the background light data falls within the preset background light data range based on the background light data sampled for n consecutive times can effectively prevent false triggering of the light adjustment operation by a peak or trough of fluctuation of the background light data when background light data sampled once happens to be at the peak or trough of the fluctuation of the background light data.

Determining whether the effective light data falls within the preset first effective light data range based on the n pieces of actual effective light data calculated based on the background light data and mixed light data sampled for n consecutive times can effectively prevent false triggering of the light adjustment operation by a peak or trough of fluctuation of the background light data or mixed light data when background light data or mixed light data sampled once happens to be at the peak or trough of the fluctuation of the background light data or mixed light data.

In the foregoing implementations of step 110, a value of n may be set based on a requirement of an actual application scenario. For example, in an application scenario, when a sampling frequency of the PPG apparatus is 25 Hz, n is set to 5 or 6.

Further, in an embodiment of the present disclosure, the preset background light data range, first effective light data range, and second effective light data range are determined based on the dynamic range of the ADC. Specifically, in an embodiment of the present disclosure, an ideal background light data range and an ideal effective light data range are determined based on the dynamic range of the ADC of the PPG apparatus. Then, the background light data range, the first effective light data range, and the second effective light data range are preset based on the ideal background light data range and the ideal effective light data range.

For example, in an application scenario, it is defined that the preset first effective light data range is [TH1, TH2]; and the preset background light data range is [BTH1, BTH2]. Assume that an ideal range of the mixed light data RawdataMix is determined based on the dynamic range of the ADC of the PPG apparatus is 10, 1310711, the background light data is fixed to a middle point 65535, and the ideal effective light data range is [0, 65535]. Based on the foregoing range values, the first effective light data range [TH1, TH2] is set to [25000, 60000], and the preset background light data range [BTH1, BTH2] is set to [45536, 85536].

If the background light data RawdataBg sampled by the PPG apparatus is greater than the upper limit BTH2 of the preset background light data range for each time of n consecutive times or less than the lower limit BTH1 of the preset background light data range for each time of several consecutive times, or the effective light data RawdataReal is greater than the upper limit TH2 of the first effective light data range for each time of n consecutive times or less than the lower limit TH1 of the first effective light data range for each time of n consecutive times, the light adjustment operation is triggered.

Further, in an embodiment of the present disclosure, the first effective light data range and the second effective light data range are a same numerical range. In another embodiment of the present disclosure, for example, in an application scenario, it is defined that the second effective light data range is [RTH1, RTH2]. The second effective light data range [RTH1, RTH2] is set to be consistent with the first effective light data range [TH1, TH2], and [RTH1, RTH2] is [25000, 60000].

Further, in actual application scenarios, a light leakage level is one of influencing factors of the PPG signal. Ideally, the light leakage level is 0. The light leakage level is generally caused by a production process. In the case of no target object, the light of the LED is reflected or refracted through a structure to a PD, resulting in a default data baseline. The default data baseline is defined as a light leakage level threshold. If the effective light data sampled by the PPG apparatus is lower than the light leakage level threshold, product performance is affected, and the production process generally needs to be improved. To avoid that the effective light data is lower than the light leakage level threshold, in another embodiment of the present disclosure, when presetting the second effective light data range, the light leakage level threshold is used as a lower limit of the second effective light data range, such that the effective light data after the light adjustment is not lower than the light leakage level threshold.

Specifically, in an embodiment of the present disclosure, if the light leakage level threshold falls within the preset first effective light data range, the lower limit of the second effective light data range is the light leakage level threshold, where the light leakage level threshold is a parameter value determined based on a light leakage status of the PPG apparatus in an application scenario. The second effective light data range is determined based on the light leakage level threshold to effectively prevent the effective light data from being lower than the light leakage level threshold, thereby ensuring the performance of the PPG apparatus.

Further, in an implementation of step 121, the preset CTR or the estimated CTR used in a last light adjustment operation is directly called to determine the estimated CTR.

Further, in an implementation of step 121, the estimated CTR is an actual CTR when the mixed light data is sampled once. Specifically, based on formula (2), the actual CTR when the PPG apparatus samples the mixed light data is calculated based on a drive current of the light source and a gain of the AFE when the mixed light data is sampled, and the calculated actual effective light data.

For example, in an implementation of step 121:

the measured effective light data during the $n^{th}$ sampling, and the drive current of the light source of the PPG and the gain of the AFE during the $n^{th}$ sampling are substituted into formula (2) to calculate the CTR. In other words, the measured effective light data, the drive current of the light source of the PPG apparatus, and the gain of the AFE during the last sampling before the light adjustment operation are substituted into formula (2) to calculate the CTR.

For example, in an application scenario, the effective light data RawdataReal$_n$ calculated during the $n^{th}$ sampling is set to 60000, and the second effective light data range is set to [32000, 43000]. During the $n^{th}$ sampling, the gain of the AFE is 50, the drive current of the light source is 80, and the adjustable range of the drive current of the light source is [0, 100].

If it is determined that the light adjustment operation is triggered, the light adjustment operation is performed. CTR=15 can be obtained based on the effective light data RawdataReal$_n$ being 60000, the gain of the AFE being 50, and the drive current of the light source being 80. In this case, the effective light data is estimated based on the estimated drive current required by the light source and gain required by the AFE by using the following formula:

$$15 \times current \times gain = RawdataReal \quad (3).$$

Further, in actual application scenarios, there may be fluctuation in sampled data when the mixed light data and background light data are sampled, and there may be fluctuation in calculation errors when the actual CTR is calculated. Therefore, when the actual CTR is calculated when the mixed light data is sampled once, there may be a quite large deviation between the calculated actual CTR and a real actual CTR. Therefore, in an implementation of step 121, the estimated CTR is an average value of a plurality of actual CTRs when the mixed light data is sampled for a plurality of times. The actual CTR when the PPG apparatus samples the mixed light data is calculated based on a drive current of the light source and a gain of the AFE when the mixed light data is sampled, and the calculated actual effective light data. The average value of the plurality of actual CTRs is used to effectively reduce the deviation between the calculated actual CTR and the real actual CTR.

For example, in an implementation of step 121:

the measured effective light data, the drive current of the light source of the PPG apparatus, and the gain of the AFE during each sampling of n consecutive samplings before the light adjustment operation are substituted into formula (2) to calculate a respective CTR corresponding to each sampling; then an average value of the calculated n CTRs is obtained.

For example, if effective light data RawdataReal is 60000, again is 50, and a current is 80 during a first sampling, then CTR=15. If effective light data RawdataReal is 62000, a gain is 50, and a current is 80 during a second sampling, then CTR=15.5. If effective light data RawdataReal is 59000, a gain is 50, and a current is 80 during a third sampling, then CTR=14.75. If effective light data RawdataReal is 61000, a gain is 50, and a current is 80 during the $n^{th}$ sampling, then CTR=15.25.

After calculation, an average value of the foregoing n CTRs is 15.05. Then, the average CTR 15.05 is used as the estimated CTR. In this case, the estimated effective light data is calculated based on the estimated drive current required by the light source and gain required by the AFE, and the estimated CTR by using the following formula:

$$15.05 \times current \times gain = RawdataReal \quad (4).$$

Further, in actual application scenarios, the PPG apparatus does not perform lighting when sampling the background light data. In other words, the setting of the drive current of the light source does not affect the acquisition of the background light data. If the background light data is beyond the preset background light data range, directly adjusting the gain of the AFE can make the PPG signal be converged within the dynamic range of the ADC as soon as possible. For example, if the sampled background light data is too large, the gain of the AFE needs to be decreased, and if the sampled background light data is too small, the gain of the AFE needs to be increased. Therefore, in an embodiment of the present disclosure, the light adjustment operation (step 120) may further include the following steps.

Before the drive current required by the light source and the gain required by the AFE are estimated (before step 122), initial adjustment is trigged if the background light data is beyond the preset background light data range. The initial adjustment includes: adjusting the gain of the AFE through convergence.

In this way, when the background light data is beyond the preset background light data range, the gain of the AFE is adjusted first to decrease the number of times the drive current required by the light source and the gain required by the AFE are estimated, thereby reducing the data processing amount, and thus obtaining as soon as possible the to-be-adjusted current/gain value for adjusting the drive current of the light source of the PPG apparatus and the gain of the AFE.

Figure 2:
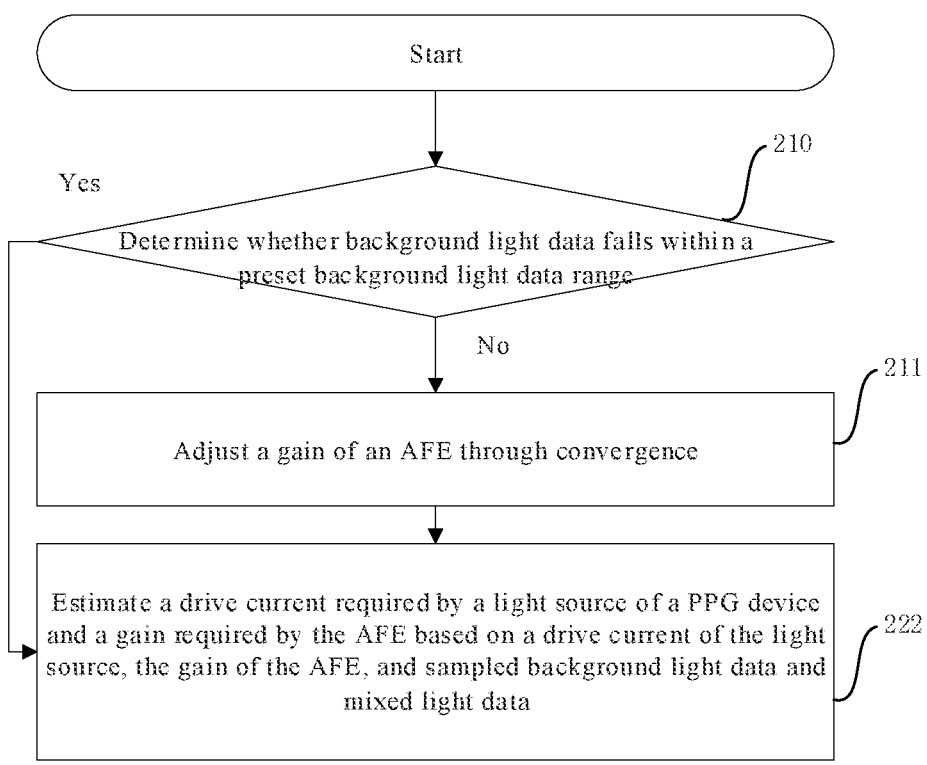
FIG. 2 is a partial flowchart of an embodiment of a signal adjustment method for a PPG apparatus according to the present disclosure.

Specifically, FIG. 2 is a partial flowchart of an embodiment of a signal adjustment method for a PPG apparatus according to the present disclosure. An embodiment of the present disclosure is as shown in FIG. 2.

Step 210: it is determined whether background light data falls within a preset background light data range.

If the background light data falls within the preset background light data range, step 222 is performed.

If the background light data is beyond the preset background light data range, step 211 is performed.

Step 211: a gain of an AFE is adjusted through convergence.

After step 211, step 222 is performed.

Step 222: a drive current required by a light source of a PPG apparatus and a gain required by the AFE are estimated based on a drive current of the light source, a gain of the AFE, and sampled background light data and mixed light data (step 122 shown in FIG. 1).

Specifically, in an implementation of step 211:
if the background light data is greater than an upper limit of the preset background light data range, then the gain of the AFE is decreased; and
if the background light data is less than a lower limit of the preset background light data range, then the gain of the AFE is increased.

Specifically, in an implementation of step 211:
if the background light data sampled for each time of n consecutive times is greater than the upper limit of the preset background light data range, the gain of the AFE is decreased by 1 before a current light adjustment operation is performed;
if the background light data sampled for each time of n consecutive times is less than a lower limit of the preset background light data range, the gain of the AFE is increased by 1 before the current light adjustment operation is performed.

Figure 3:
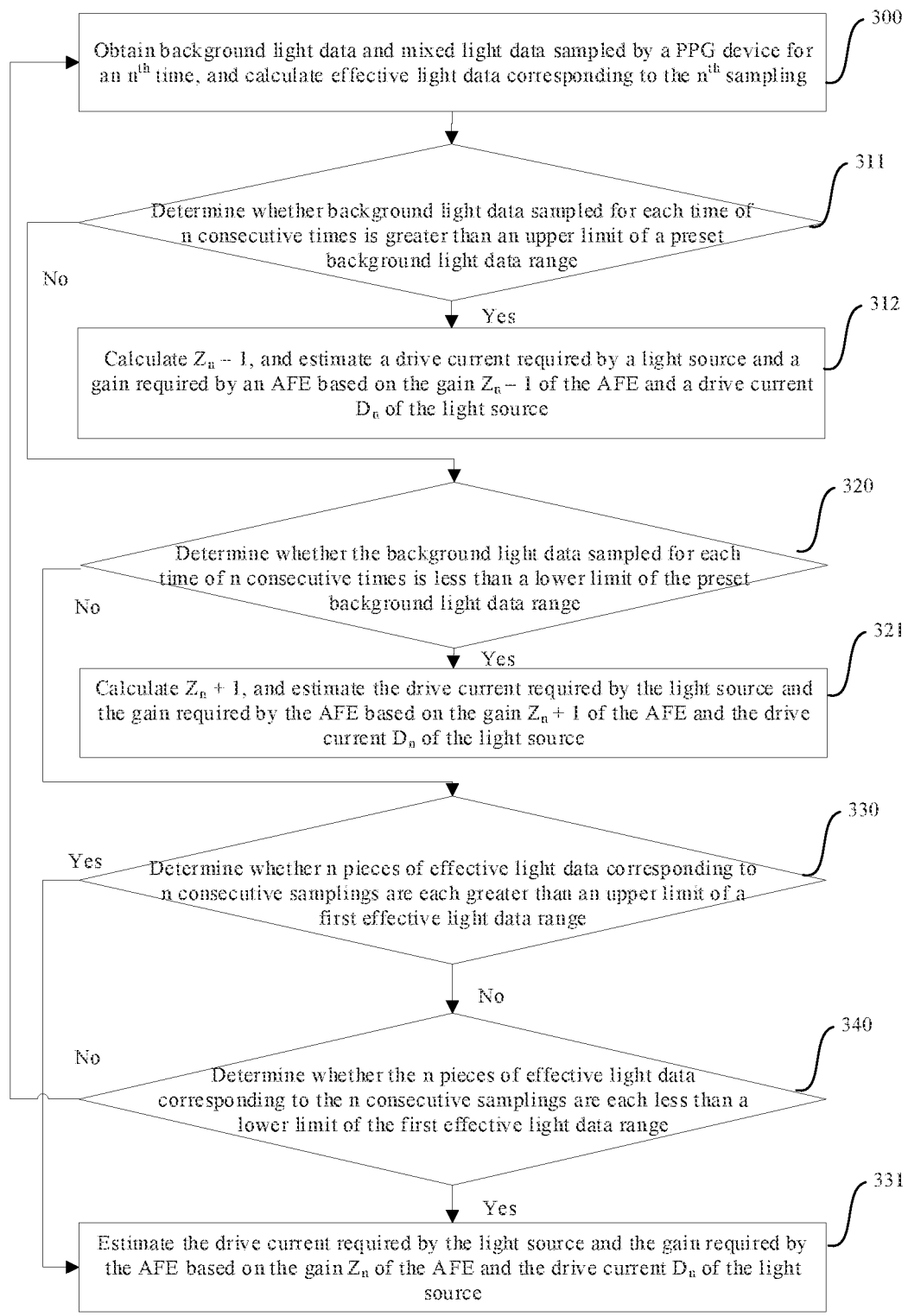
FIG. 3 is a flowchart of an embodiment of a signal adjustment method for a PPG apparatus according to the present disclosure.

Specifically, FIG. 3 is a partial flowchart of an embodiment of a signal adjustment method for a PPG apparatus according to the present disclosure. In an embodiment of the present disclosure, assume that before a light adjustment operation is performed, a gain of an AFE is $Z_n$, and a drive current of a light source is $D_n$. As shown in FIG. 3, a PPG apparatus performs the following steps.

Step 300: background light data and mixed light data sampled by the PPG apparatus for an $n^{th}$ time are obtained, and effective light data corresponding to the n sampling is calculated.

Step 311: it is determined whether background light data sampled for each time of n consecutive times is greater than an upper limit of a preset background light data range.

If the background light data sampled for each time of n consecutive times is greater than the upper limit of the preset background light data range, step 312 is performed.

Step 312: $Z_n-1$ is calculated, and a drive current required by the light source and a gain required by the AFE are estimated based on the gain $Z_n-1$ of the AFE and the drive current Da of the light source.

If a determining result of step 311 is no, step 320 is performed.

Step 320: it is determined whether the background light data sampled for each time of n consecutive times is less than a lower limit of the preset background light data range.

If the background light data sampled for each time of n consecutive times is less than the lower limit of the preset background light data range, step 321 is performed.

Step 321: $Z_n+1$ is calculated, and the drive current required by the light source and the gain required by the AFE are estimated based on the gain $Z_n+1$ of the AFE and the drive current $D_n$ of the light source.

If a determining result of step 320 is no, step 330 is performed.

Step 330: it is determined whether n pieces of effective light data corresponding to n consecutive samplings are each greater than an upper limit of a first effective light data range.

If the n pieces of effective light data corresponding to the n consecutive samplings are each greater than the upper limit of the first effective light data range, step 331 is performed.

Step 331: the drive current required by the light source and the gain required by the AFE are estimated based on the gain $Z_n$ of the AFE and the drive current $D_n$ of the light source.

If a determining result of step 330 is no, step 340 is performed.

Step 340: it is determined whether n pieces of effective light data corresponding to n consecutive samplings are each less than a lower limit of the first effective light data range.

If the n pieces of effective light data corresponding to the n consecutive samplings are each less than the lower limit of the first effective light data range, step 331 is performed.

If a determining result of step 340 is no, step 300 is performed.

Further, in an embodiment of the present disclosure, considering that adjustability of the drive current of the light source is better than that of the gain of the AFE, the drive current of the light source is preferentially adjusted. Therefore, in step 122, in the process of estimating the drive current required by the light source and the gain required by the AFE, the drive current is estimated first, and the gain is estimated only when the drive current reaches an upper limit or a lower limit of a preset adjustable current range and the estimated effective light data still cannot fall within a second effective light data range.

Specifically, in an implementation of step 122:
if the drive current of the light source falls within the preset adjustable current range of the PPG apparatus, the drive current of the light source is adjusted;
if the drive current of the light source is beyond the preset adjustable current range of the PPG apparatus, and the gain of the AFE falls within the preset adjustable gain range of the PPG apparatus, the gain of the AFE is adjusted.

Figure 4:
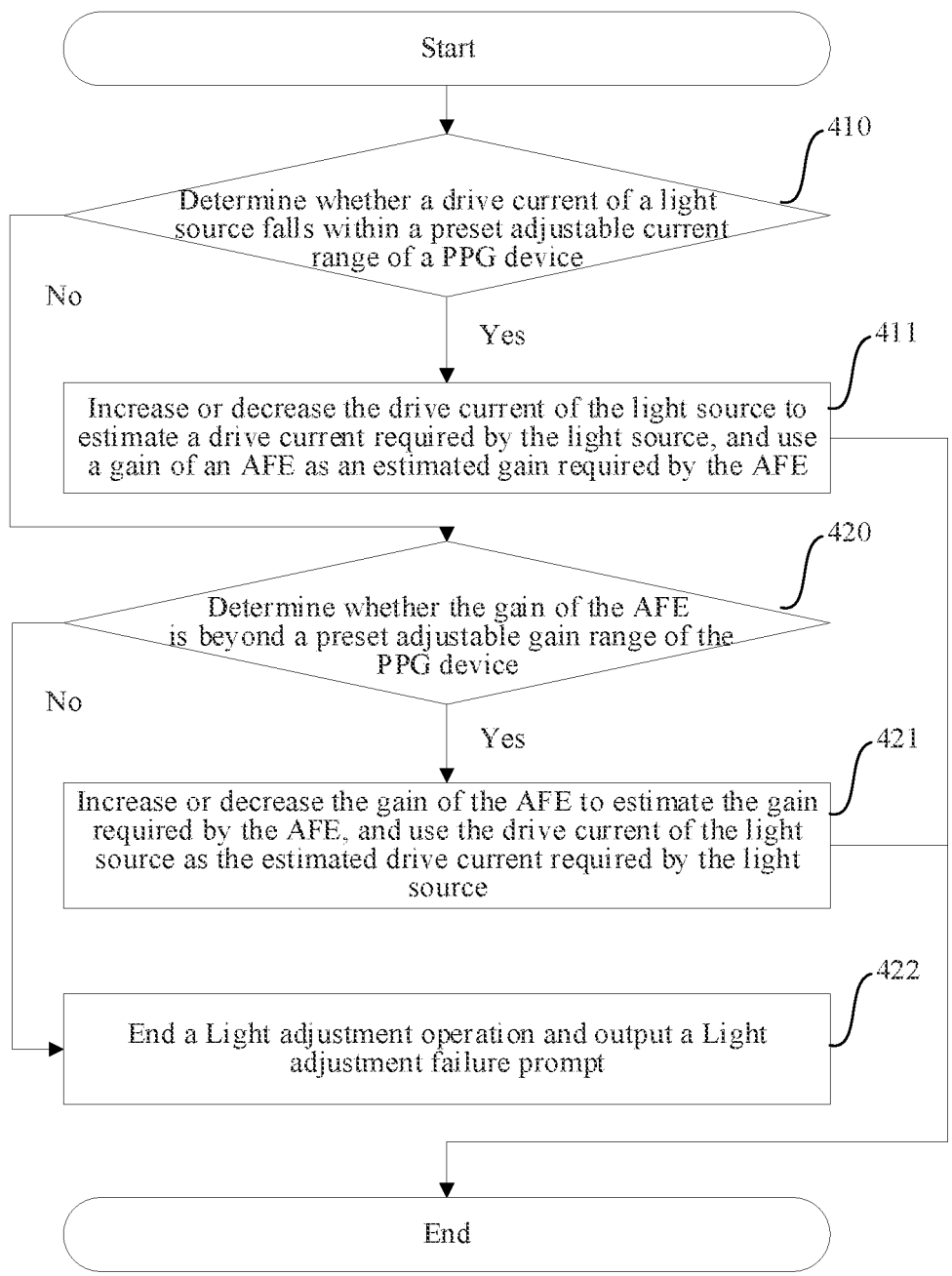
FIG. 4 is a partial flowchart of an embodiment of a signal adjustment method for a PPG apparatus according to the present disclosure.

Specifically, FIG. 4 is a partial flowchart of an embodiment of a signal adjustment method for a PPG apparatus according to the present disclosure. In an embodiment of the present disclosure, as shown in FIG. 4, a PPG apparatus performs the following steps to implement step 122 shown in FIG. 1.

Step 410: it is determined whether a drive current of a light source falls within a preset adjustable current range of the PPG apparatus. In other words, when the drive current of the light source needs to be increased, it is judged whether the drive current is equal to an upper limit of the adjustable current range, or when the drive current of the light source needs to be decreased, it is judged whether the drive current is equal to a lower limit of the adjustable current range.

If the drive current of the light source falls within the preset adjustable current range of the PPG apparatus, step 411 is performed.

Step 411: the drive current of the light source is increased or decreased to estimate a drive current required by the light source, and the gain of the AFE is used as an estimated gain required by the AFE.

If the drive current of the light source is beyond the preset adjustable current range of the PPG apparatus, step 420 is performed.

Step 420: it is determined whether the gain of the AFE falls within a preset adjustable gain range of the PPG apparatus. In other words, when the gain of the AFE needs to be increased, it is judged whether the gain of the AFE is equal to an upper limit of the adjustable gain range, or when the gain of the AFE needs to be decreased, it is judged whether the gain of the AFE is equal to a lower limit of the adjustable gain range.

If the gain of the AFE falls within the preset adjustable gain range of the PPG apparatus, step 421 is performed.

Step 421: the gain of the AFE is increased or decreased to estimate the gain required by the AFE, and the drive current of the light source is used as the estimated drive current required by the light source.

If the gain of the AFE is beyond the preset adjustable gain range of the PPG apparatus, step 422 is performed.

Step 422: a light adjustment operation ends, and a light adjustment failure prompt is output.

Further, in an embodiment of the present disclosure, when re-estimating the drive current required by the light source and the gain required by the AFE, a method of prioritizing the drive current is also used. Specifically, in an embodiment of the present disclosure, the process shown in FIG. 4 is executed in step 126 shown in FIG. 1.

Further, in an embodiment of the present disclosure, to quickly generate a to-be-adjusted current/gain value, the drive current required by the light source is estimated through dichotomization. Estimating the drive current required by the light source through dichotomization can not only quickly estimate the drive current required by the light source, but also effectively reduce the number of times the drive current required by the light source is re-estimated.

Specifically, in an implementation of step 411:
when the drive current of the light source needs to be increased, the following formula is used:

Estimated drive current=(Drive current+Upper limit of the adjustable current range)/2     (5):

when the drive current of the light source needs to be decreased, the following formula is used:

Estimated drive current=(Drive current+Lower limit of the adjustable current range)/2     (6).

For example, in an application scenario, effective light data RawdataReal$_n$ corresponding to an $n^{th}$ sampling is set to 60000, and a second effective light data range is set to [32000, 43000]. During the $n^{th}$ sampling, the gain of the AFE is 50, the drive current of the light source is 80, and the adjustable range of the drive current of the light source is [0, 100].

If it is determined that the light adjustment operation is triggered, it is obtained that CTR=15 based on the effective light data RawdataReal$_n$ being 60000, the gain of the AFE being 50, and the drive current of the light source being 80. A function for calculating the effective light is as follows:

15×current×gain=RawdataReal     (7).

Initial adjustment is not triggered, and the drive current of the light source is preferentially adjusted through dichotomization.

The drive current of the light source is 80, and the lower limit of the adjustable range of the drive current of the light source is 0. In this case, the drive current required by the light source is estimated to be 40 through dichotomization. When it is assumed that the drive current of the light source is 40 and the gain of the AFE is 50. 'RawdataReal is 30000 based on CTR=15. When 'RawdataReal is 30000, 'RawdataReal is lower than a lower limit 32000 of the second effective light data range. Therefore, the drive current required by the light source needs to be re-estimated.

The drive current of the light source is 40, and the upper limit of the adjustable range of the drive current of the light source is 100. In this case, the drive current required by the light source is re-estimated to be 70 through dichotomization. When it is assumed that the drive current of the light source is 70 and the gain of the AFE is 50, 'RawdataReal is 52500 based on CTR=15. When 'RawdataReal is 52500. 'RawdataReal is higher than an upper limit 43000 of the second effective light data range. Therefore, the drive current required by the light source needs to be re-estimated.

The drive current of the light source is 70, and the lower limit of the adjustable range of the drive current of the light source is 0. In this case, the drive current required by the light source is re-estimated to be 35 through dichotomization.

The foregoing steps of the dichotomization are cyclically performed. Finally, when the estimated drive current of the light source is 50 and the gain of the AFE is 50, 'RawdataReal is 37500. In this case, 'RawdataReal falls within the second effective light data range [32000, 43000]. The to-be-adjusted current/gain value is generated based on the drive current 50 of the light source and the gain 50 of the AFE, to complete the light adjustment.

Further, in an embodiment of the present disclosure, to quickly generate the to-be-adjusted current/gain value, the drive current required by the light source is estimated through stepping. Estimating the drive current required by the light source through stepping can not only quickly estimate the drive current required by the light source, but also effectively reduce a data processing amount for estimating the drive current required by the light source.

For example, in an implementation of step 411:
when the drive current of the light source needs to be increased, the following formula is used:

Estimated drive current=Drive current+Preset current step     (8);

when the drive current of the light source needs to be decreased, the following formula is used:

Estimated drive current=Drive current−Preset current step     (9).

For example, in an application scenario, effective light data RawdataReal$_n$ corresponding to an $n^{th}$ sampling is 60000, and a second effective light data range is set to [32000, 43000]. During the $n^{th}$ sampling, the gain of the AFE is 50, the drive current of the light source is 80, and the adjustable range of the drive current of the light source is 10, 1001.

If it is determined that the light adjustment operation is triggered, it is obtained that CTR=15 based on the effective light data RawdataReal$_n$ being 60000, the gain of the AFE being 50, and the drive current of the light source being 80. A function for calculating the effective light is as follows:

15×current×gain=RawdataReal     (10).

Initial adjustment is not triggered, and the drive current of the light source is preferentially estimated through stepping.

The drive current of the light source is 80, and the preset step is 1. In this case, the drive current required by the light source is estimated to be 79. When it is assumed that the drive current of the light source is 79 and the gain of the AFE is 50. 'RawdataReal is 59250 based on CTR=15. When 'RawdataReal is 59250, 'RawdataReal is higher than an upper limit 43000 of the second effective light data range. Therefore, the drive current required by the light source needs to be re-estimated.

The drive current of the light source is 79, and the preset step is 1. In this case, the drive current required by the light source is estimated to be 78.

The foregoing steps of the stepping are cyclically performed. Finally, when the estimated drive current of the light source is 57, and the gain of the AFE is 50, 'RawdataReal is 42750. In this case, 'RawdataReal falls within the second effective light data range [32000, 43000]. The to-be-adjusted current/gain value is generated based on the drive current 57 of the light source and the gain 50 of the AFE, to complete the light adjustment.

Further, in an embodiment of the present disclosure, to quickly generate a to-be-adjusted current/gain value, the gain required by the AFE is estimated through dichotomization. Estimating the gain required by the AFE through dichotomization can not only quickly estimate the gain required by the AFE, but also effectively reduce the number of times the gain required by the AFE is re-estimated.

For example, in an implementation of step 411:
when the gain of the AFE needs to be increased, the following formula is used:

$$\text{Estimated gain}=(\text{Gain}+\text{Upper limit of the adjustable gain range})/2 \quad (11);$$

when the drive current of the light source needs to be decreased, the following formula is used:

$$\text{Estimated gain}=(\text{Gain}+\text{Lower limit of the adjustable gain range})/2 \quad (12).$$

Further, in an embodiment of the present disclosure, to quickly generate a to-be-adjusted current/gain value and reduce the number of times the gain required by the AFE is re-estimated, the gain required by the AFE is estimated through stepping. Estimating the gain required by the AFE through stepping can not only quickly estimate the gain required by the AFE, but also effectively reduce a data processing amount for estimating the gain required by the AFE.

In an implementation of step 411:
when the gain of the AFE needs to be increased, the following formula is used:

$$\text{Estimated gain}=\text{Gain}+1 \quad (13):$$

when the gain of the AFE needs to be decreased, the following formula is used:

$$\text{Estimated gain}=\text{Gain}-1 \quad (14).$$

The following describes a process of a method in an embodiment of the present disclosure by using a specific application scenario as an example. In an application scenario in an embodiment of the present disclosure, it is assumed that a first effective light data range is [TH1, TH2], an adjustable current range of a drive current of an LED is [D1, D2], an adjustable gain range of a gain of an AFE is [G1, G2], the drive current of the LED is $D_n$, and the gain of the AFE is $Z_n$.

Step (1.1)
If effective light data RawdataReal is greater than TH2 for each time of n consecutive times, the drive current of the LED or the gain of the AFE needs to be decreased.

Step (1.2)
If $D_n$ is greater than D1, dichotomization is performed.

$$D_n1=(D_n+D1)/2 \quad (15).$$

Assuming that a second effective light data range is [RTH1, RTH2], 'RawdataReal$_1$ is calculated based on $D_n1$ and $Z_n$, and it is determined whether 'RawdataReal$_1$ falls within [RTH1, RTH2].

Step (1.3)
If 'RawdataReal$_1$ falls within [RTH1, RTH2], a to-be-adjusted current/gain value is generated based on $D_n1$ and $Z_n$.

Step (1.4)
If 'RawdataReal$_1$>RTH2, and $D_n1$ is greater than D1, $D_n$ is replaced with $D_n1$ and steps (1.2) to (1.4) are performed again.

If $D_n1$ is equal to D1, it is determined whether $Z_n$ is greater than G1.

If $Z_n$ is equal to G1, it is determined that light adjustment fails, and the light adjustment ends.

Step (1.5)
If $Z_n$ is greater than G1, the following formula is calculated: $Z_n1=Z_n-1$.

'RawdataReal$_2$ is calculated based on $D_n1$ and $Z_n1$, and it is determined whether 'RawdataReal$_2$ falls within [RTH1, RTH2].

Step (1.6)
If 'RawdataReal$_2$ falls within [RTH1, RTH2], a to-be-adjusted current/gain value is generated based on $D_n1$ and $Z_n1$.

Step (1.7)
If 'RawdataReal$_2$>RTH2, and $Z_n1$ is greater than G1, $Z_n$ is replaced with $Z_n1$ and steps (1.5) to (1.7) are performed again.

If $Z_n1$ is equal to G1, it is determined that light adjustment fails, and the light adjustment ends.

Step (2.1)
If RawdataReal is less than TH1 for each time of n consecutive times, the drive current of the LED or the gain of the AFE needs to be increased.

Step (2.2)
If $D_n$ is less than D2, dichotomization is performed.

$$D_n2=(D_n+D1)/2 \quad (16).$$

Assuming that the second effective light data range is [RTH1. RTH2], 'RawdataReal$_3$ is calculated based on $D_n2$ and $Z_n$, and it is determined whether 'RawdataReal$_3$ falls within [RTH1, RTH2].

Step (2.3)
If 'RawdataReal$_3$ falls within [RTH1, RTH2], a to-be-adjusted current/gain value is generated based on $D_n2$ and $Z_n$.

Step (2.4)
If 'RawdataReal$_3$<RTH1, and $D_n2$ is less than D2, $D_n$ is replaced with $D_n2$ and steps (2.2) to (2.4) are performed again.

If $D_n2$ is equal to D2, it is determined whether $Z_n$ is less than G2.

If $Z_n$ is equal to G2, it is determined that light adjustment fails, and the light adjustment ends.

Step (2.5)
If $Z_n$ is less than G2, the following formula is calculated:

$$Z_n2=Z_n+1 \quad (17).$$

'RawdataReal$_4$ is calculated based on $D_n2$ and $Z_n2$, and it is determined whether 'RawdataReal$_4$ falls within [RTH1, RTH2].

Step (2.6)
If 'RawdataReal$_4$ falls within [RTH1, RTH2], a to-be-adjusted current/gain value is generated based on $D_n2$ and $Z_n2$.

Step (2.7)
If 'RawdataReal$_4$<RTH1, and $Z_n2$ is less than G2, $Z_n$ is replaced with $Z_n2$ and steps (2.5) to (2.7) are performed again.

If $Z_n2$ is equal to G2, it is determined that light adjustment fails, and the light adjustment ends.

Further, in an implementation of step 125, in the process of generating the to-be-adjusted current/gain value based on the estimated drive current required by the light source and the gain required by the AFE, the estimated drive current required by the light source and the gain required by the AFE are directly used as the to-be-adjusted current/gain value.

Further, in actual application scenarios, the influencing factors of the PPG signal also include apparatus jitter (for example, jitter of the PPG apparatus caused by a wearer's movement). The jitter of the PPG apparatus increases the fluctuation of the sampled background light data and the effective light data. This makes a first current and a first gain determined by using the function for calculating the effective light are greater than those in a non-jitter state. Therefore, in an embodiment of the present disclosure, the estimated drive current required by the light source and gain required by the AFE are not directly used as the to-be-adjusted current/gain value. The estimated drive current required by the light source and gain required by the AFE are further adjusted based on a jitter status of the PPG apparatus.

Specifically, in an implementation of step 125:
an apparatus jitter parameter of the PPG apparatus is obtained;
a corresponding attenuation coefficient is called or calculated based on the apparatus jitter parameter; and
attenuation calculation is performed on the estimated drive current required by the light source and gain required by the AFE based on the attenuation coefficient, and a result of the attenuation calculation is used as the to-be-adjusted current/gain value.

Specifically, in an embodiment of the present disclosure, the attenuation calculation is to multiply the estimated drive current required by the light source and/or gain required by the AFE by the attenuation coefficient.

For example, in an application scenario, jitter data of the PPG apparatus is obtained through a motion sensor to calculate jitter amplitude A. A corresponding attenuation coefficient is called based on the jitter amplitude A. Specifically, a plurality of different jitter amplitude ranges are defined, and the ranges are used for grading, and different grades correspond to different attenuation coefficients. A grade corresponding to the jitter amplitude A is determined, and an attenuation coefficient corresponding to the grade is further called.

For another example, in an application scenario, jitter data of the PPG apparatus is obtained through a motion sensor to calculate jitter amplitude A. A motion compensation calculation parameter is calculated based on the jitter amplitude A. Specifically, in this application scenario, a sigmoid function (Sigmoid) is multiplied by the jitter amplitude A, a normalization algorithm (Normalization) is used to normalize the foregoing product, and an attenuation coefficient is calculated based on a normalization result. The attenuation coefficient is calculated by using the formula:

$$\text{Attenuation coefficient} = 1 - 0.7 \times \text{Normalization}(A \times \text{Siginoid}) \quad (18).$$

Further, in actual application scenarios, there may be a deviation between the effective light data calculated based on the estimated drive current required by the light source and gain required by the AFE and the effective light data obtained after the drive current of the light source and the gain of the AFE are set to the estimated drive current required by the light source and gain required by the AFE and the PPG apparatus performs sampling and calculation. In other words, in some application scenarios, the effective light data calculated based on the estimated drive current required by the light source and gain required by the AFE falling within the second effective light data range does not mean that the effective light data obtained after the drive current of the light source and the gain of the AFE are set to the estimated drive current required by the light source and gain required by the AFE and the PPG apparatus performs sampling and calculation also falls within the second effective light data range. After the light adjustment operation, the PPG signal may still not be converged within the dynamic range of the ADC.

In view of the foregoing situation, in an embodiment of the present disclosure, sampling and measurement of the effective light data is performed after the light adjustment operation is completed. If the measured effective light data cannot fall within the second effective light data range, the light adjustment operation is performed again. The light adjustment operation is repeatedly performed until the measured effective light data falls within the second effective light data range or both the drive current of the light source and the gain of the AFE are beyond the preset adjustable current and gain ranges.

Specifically, in an embodiment of the present disclosure, after step 120, the method further includes the following steps.

Sampling verification is performed. The sampling verification includes: after the drive current of the light source of the PPG apparatus and the gain of the AFE are adjusted based on the to-be-adjusted current/gain value, obtaining background light data and mixed light data, and recalculating the actual effective light data based on the obtained background light data and mixed light data.

If the recalculated actual effective light data is beyond the second effective light data range, the light adjustment operation and the sampling verification are cyclically performed.

Figure 5:
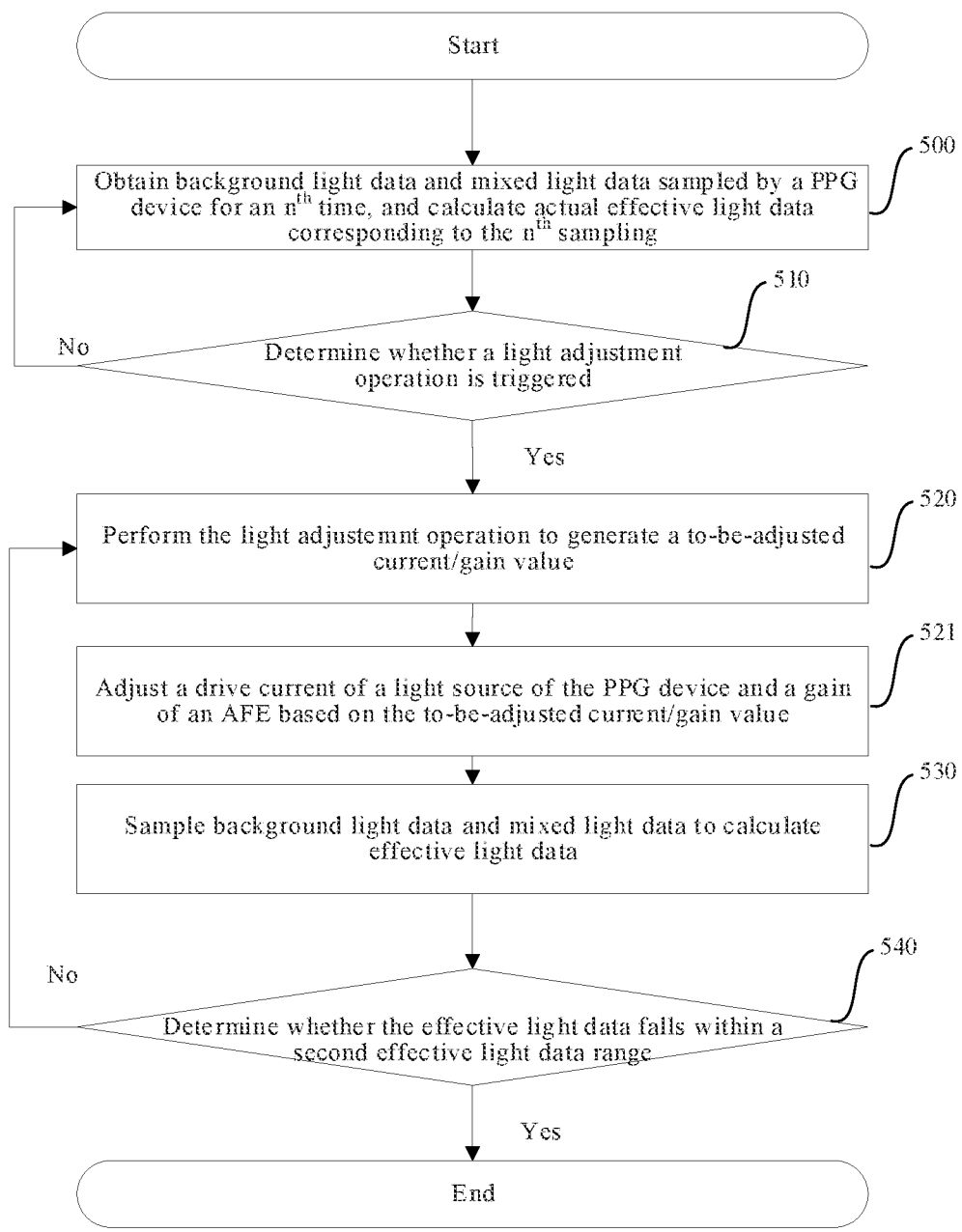
FIG. 5 is a flowchart of an embodiment of a signal adjustment method for a PPG apparatus according to the present disclosure.

FIG. 5 is a flowchart of an embodiment of a signal adjustment method for a PPG apparatus according to the present disclosure. In an embodiment of the present disclosure, as shown in FIG. 5, the method includes following steps.

Step 500: background light data and mixed light data sampled by a PPG apparatus for an $n^{th}$ time are obtained, and actual effective light data corresponding to the $n^{th}$ sampling are calculated (n is a natural number greater than zero).

Step 510: it is determined whether the light adjustment operation is triggered based on the background light data sampled for the $n^{th}$ time and/or the effective light data corresponding to the $n^{th}$ sampling.

If the light adjustment operation is not triggered, step 500 is performed again.

If the light adjustment operation is triggered, step 520 is performed.

Step 520: the light adjustment operation is performed to generate a to-be-adjusted current/gain value.

Step 521: a drive current of a light source of the PPG apparatus and a gain of an AFE are adjusted based on the to-be-adjusted current/gain value.

Step 530: background light data and mixed light data are sampled to calculate effective light data.

Step 540: it is determined whether the effective light data calculated in step 530 falls within a second effective light data range.

If yes, the light adjustment ends.

If no, step 520 is performed again.

Further, in an implementation of the embodiment shown in FIG. 5, when step 520 is performed for a first time after it is determined that the light adjustment operation is triggered in step 510, in step 520, a CTR is calculated based on the drive current of the light source and the gain of the AFE when the PPG apparatus performs sampling, and the calculated actual effective light data. In step 540, when it is determined that the effective light data is beyond the second effective light data range, and step 520 needs to be performed again, the CTR is not recalculated in this execution of step 520, and the CTR used in a last execution of step 520 is directly called.

For example, in an application scenario, the effective light data RawdataReal$_n$ corresponding to the $n^{th}$ sampling is 60000, and the second effective light data range is set to [32000, 43000]. During the $n^{th}$ sampling, the gain of the AFE is 50, the drive current of the light source is 80, and the adjustable range of the drive current of the light source is [0, 100].

When it is determined that first light adjustment is not triggered and second light adjustment is triggered, the light adjustment operation is performed. It is obtained CTR=15 based on RawdataReal$_n$ being 60000, the gain of the AFE being 50, and the drive current of the light source being 80.

Initial adjustment is not performed on the gain of the AFE, and the drive current of the light source is preferentially adjusted. Finally, when the estimated drive current of the light source is 57, and the gain of the AFE is 50, 'RawdataReal is 42750. In this case, 'RawdataReal falls within the second effective light data range [32000, 43000]. The drive current of the light source of the PPG apparatus is set to 57 and the gain of the AFE is set to 50, to complete the first light adjustment operation.

After the drive current of the light source of the PPG apparatus is set to 57 and the gain of the AFE is set to 50, an $(n+1)^{th}$ sampling is performed to obtain RawdataReal$_{n+1}$=43100. RawdataReal$_{n+1}$=43100, which is greater than an upper limit 43000 of the second effective light data range. Therefore, the light adjustment operation is performed again.

During the second light adjustment operation, initial adjustment is not performed on the gain of the AFE, and the drive current of the light source is preferentially adjusted. CTR=15 obtained during the first light adjustment operation is used. Finally, when the estimated drive current of the light source is 50, and the gain of the AFE is 50, 'RawdataReal is 37500. In this case, 'RawdataReal falls within the second effective light data range [32000, 43000]. The drive current of the light source of the PPG apparatus is set to 50 and the gain of the AFE is set to 50, to complete the second light adjustment operation.

After the drive current of the light source of the PPG apparatus is set to 50 and the gain of the AFE is set to 50, an $(n+2)^{th}$ sampling is performed to obtain RawdataReal$_{n+2}$=37600. RawdataReal$_{n+2}$=37600 falls within the second effective light data range [32000, 43000]. Therefore, the light adjustment ends.

Figure 6:
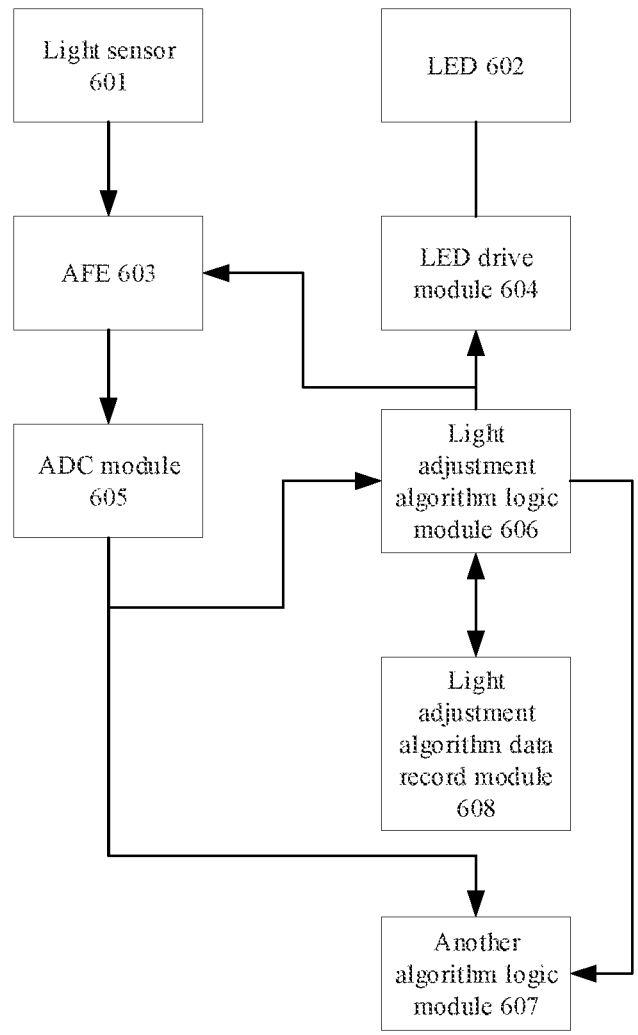
FIG. 6 is a schematic structural diagram of a PPG apparatus according to an embodiment of the present disclosure.

A specific application scenario is used as an example. FIG. 6 is a schematic structural diagram of a PPG apparatus according to an embodiment of the present disclosure. As shown in FIG. 6, an LED drive module 604 outputs a drive current to an LED 602 to drive the LED 602 to emit light. A light sensor 601 acquires external light data (background light data and mixed light data) and outputs the acquired external light data to an AFE 603. The AFE 603 outputs the external light data to an ADC module 605. The ADC module 605 performs analog-to-digital conversion on the received external light data, and outputs a conversion result to a light adjustment algorithm logic module 606.

The light adjustment algorithm logic module 606 determines whether to perform light adjustment based on the data output from the ADC module 605.

During the light adjustment, the light adjustment algorithm logic module 606 estimates a drive current required by the LED 602 and a gain required by the AFE 603 based on the drive current output from the LED drive module 604 and a gain of the AFE 603. After the estimation is completed, the light adjustment algorithm logic module 606 adjusts the LED drive module 604 such that the output drive current is the estimated drive current; and adjusts the AFE 603 such that the gain of the AFE is the estimated gain.

Further, during the light adjustment, the light adjustment algorithm logic module 606 performs data interaction with a light adjustment algorithm data record module 608, for example, calling or recording a value of CTR.

Further, during the light adjustment, the light adjustment algorithm logic module 606 outputs a light adjustment failure flag bit to another algorithm logic module 607 when the light adjustment fails.

Further, after the light adjustment is completed, the another algorithm logic module 607 obtains the external light data from the ADC module 605 to perform another data processing operation, such as analyzing blood vessel pulsation.

It can be understood that some or all of the steps or operations in the foregoing embodiments are merely examples, and other operations or variants of various operations can further be performed in the embodiments of the present disclosure. In addition, the steps may be performed in different orders presented in the foregoing embodiments, and not all the operations in the foregoing embodiments need to be performed.

Figure 7:
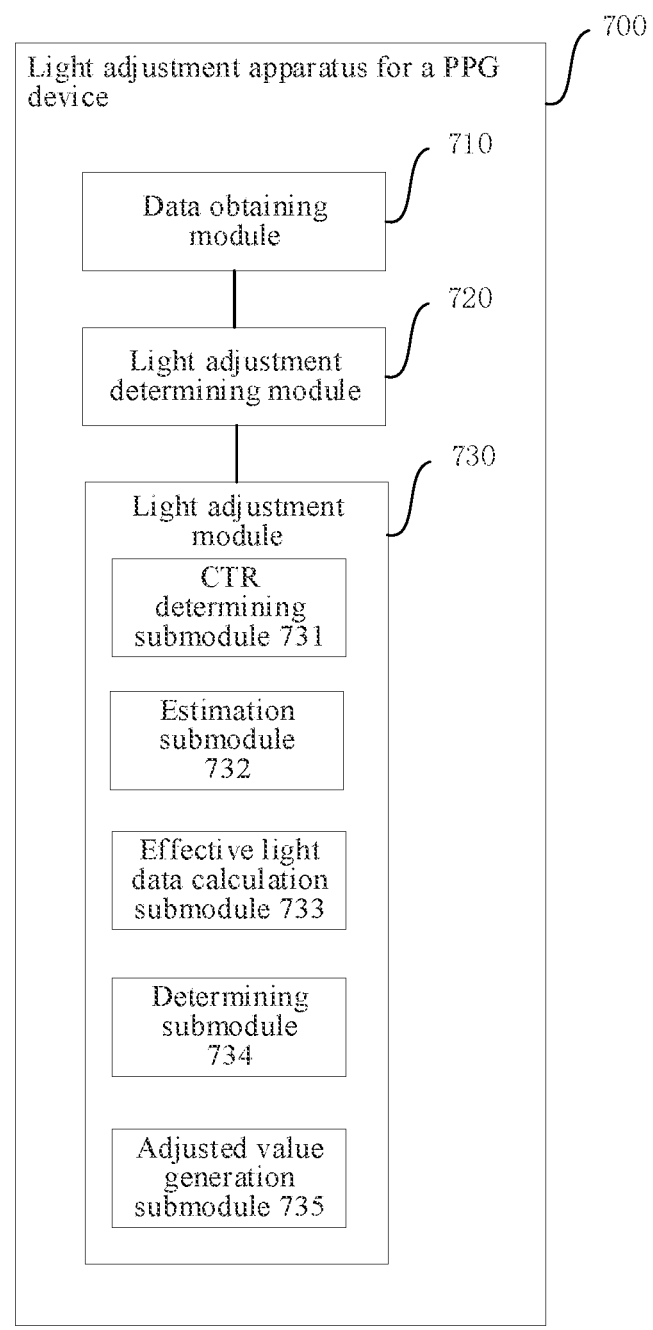
FIG. 7 is a structural diagram of an embodiment of a light adjustment apparatus for a PPG apparatus according to the present disclosure.

Further, according to the signal adjustment method for a PPG apparatus in the embodiments of the present disclosure, an embodiment of the present disclosure further provides a light adjustment apparatus for a PPG apparatus. Specifically, FIG. 7 is a structural diagram of an embodiment of a light adjustment apparatus for a PPG apparatus according to the present disclosure. In an embodiment of the present disclosure, as shown in FIG. 7, a light adjustment apparatus 700 for a PPG apparatus includes:

a data obtaining module 710, configured to sample background light data and mixed light data;

a light adjustment determining module 720, configured to determine whether the background light data falls within a preset background light data range based on the background light data, and/or determine whether calculated actual effective light data falls within a preset first effective light data range based on calculated actual effective light data, where the actual effective light data is a difference between the mixed light data and the background light data; and a light adjustment module 730, configured to perform a light adjustment operation if the background light data is beyond the preset background light data range, or the actual effective light data is beyond the preset first effective light data range.

The light adjustment module 730 includes:

a CTR determining submodule 731, configured to determine an estimated CTR based on a preset CTR or an actual CTR of a PPG apparatus;

an estimation submodule 732, configured to estimate a drive current required by a light source of the PPG apparatus and a gain required by an AFE based on a drive current of the light source, a gain of the AFE, and the sampled background light data and mixed light data;

an effective light data calculation submodule 733, configured to calculate estimated effective light data of the PPG apparatus based on the estimated drive current required by the light source, the estimated gain required by the AFE, and the estimated CTR;

a determining submodule 734, configured to determine whether the estimated effective light data falls within a preset second effective light data range; and an adjusted value generation submodule 735, configured to: if the estimated effective light data falls within the preset second effective light data range, generate a to-be-adjusted current/gain value based on the estimated drive current required by the light source and gain required by the AFE to adjust the drive current of the light source of the PPG apparatus and the gain of the AFE.

Further, in an embodiment of the present disclosure;

the estimation submodule 732 is further configured to: if the estimated effective light data is beyond the preset second effective light data range, re-estimate the drive current required by the light source and the gain required by the AFE through convergence based on the currently estimated drive current required by the light source and gain required by the AFE to recalculate the estimated effective light data.

The determining submodule 734 is further configured to determine whether the recalculated estimated effective light data falls within the preset second effective light data range.

The adjusted value generation submodule 735 is further configured to: if the recalculated estimated effective light data falls within the preset second effective light data range, generate a to-be-adjusted current/gain value based on the re-estimated drive current required by the light source and gain required by the AFE.

Further, in an embodiment of the present disclosure:

the estimation submodule 732 is further configured to: if the recalculated estimated effective light data is beyond the preset second effective light data range, and the currently estimated drive current and gain fall within a preset adjustable current range and adjustable gain range of the PPG apparatus respectively, re-estimate the drive current required by the light source and the gain required by the AFE through convergence.

Further, in an embodiment of the present disclosure:

the estimation submodule 732 is further configured to end the light adjustment operation if the recalculated estimated effective light data is beyond the preset second effective light data range, and the currently estimated drive current and gain are beyond the preset adjustable current range and adjustable gain range respectively.

Further, in an embodiment of the present disclosure, the light adjustment module 730 further includes an initial adjustment submodule.

The initial adjustment submodule is configured to: before the drive current required by the light source and the gain required by the AFE are estimated during the light adjustment operation, trigger initial adjustment if the background light data is beyond the preset background light data range. The initial adjustment includes: adjusting the gain of the AFE through convergence.

Specifically, in an embodiment of the present disclosure, the initial adjustment submodule adjusting the gain of the AFE through convergence includes the following steps.

If the background light data is greater than an upper limit of the preset background light data range, the gain of the AFE is decreased.

If the background light data is less than a lower limit of the preset background light data range, the gain of the AFE is increased.

Specifically, in an embodiment of the present disclosure, the estimation submodule 732 estimates the drive current required by the light source and the gain required by the AFE through dichotomization or stepping.

Specifically, in an embodiment of the present disclosure, the estimation submodule 732 estimating the drive current required by the light source and the gain required by the AFE includes the following steps.

If the drive current of the light source falls within the preset adjustable current range of the PPG apparatus, the drive current of the light source is adjusted.

If the drive current of the light source is beyond the preset adjustable current range of the PPG apparatus, and the gain of the AFE falls within the preset adjustable gain range of the PPG apparatus, the gain of the AFE is adjusted.

Specifically, in an embodiment of the present disclosure, the CTR determining submodule 731 determining the estimated CTR based on the actual CTR of the PPG apparatus includes the following steps.

The estimated CTR is an actual CTR when the mixed light data is sampled for one time, or an average value of a plurality of actual CTRs when the mixed light data is sampled for a plurality of times. The actual CTR when the PPG apparatus samples the mixed light data is calculated based on a drive current of the light source and a gain of the AFE when the mixed light data is sampled, and the calculated actual effective light data.

Specifically, in an embodiment of the present disclosure, the light adjustment determining module 720 determining whether the background light data falls within the preset background light data range includes the following steps.

If background light data sampled for an $n^{th}$ time or for each time of n consecutive times is beyond the preset background light data range, it is determined that the background light data is beyond the preset background light data range.

Specifically, in an embodiment of the present disclosure, the light adjustment determining module 720 determining whether the calculated effective light data falls within the preset first effective light data range includes the following steps.

If effective light data calculated for the $n^{th}$ time or for each time of n consecutive times is beyond the preset first effective light data range, it is determined that the effective light data is beyond the preset first effective light data range.

Specifically, in an embodiment of the present disclosure, if a light leakage level threshold falls within the preset first effective light data range, a lower limit of the second effective light data range used by the determining submodule 734 is the light leakage level threshold, where the light leakage level threshold is a parameter value determined based on a light leakage status of the PPG apparatus in an application scenario.

Specifically, in an embodiment of the present disclosure, the adjusted value generation submodule 735 generating the to-be-adjusted current/gain value based on the estimated drive current required by the light source and gain required by the AFE includes the following steps.

An apparatus jitter parameter of the PPG apparatus is obtained.

A corresponding attenuation coefficient is called or calculated based on the apparatus jitter parameter.

Attenuation calculation is performed on the estimated drive current required by the light source and gain required by the AFE based on the attenuation coefficient, and a result of the attenuation calculation is used as the to-be-adjusted current/gain value.

Further, in an embodiment of the present disclosure, the apparatus 700 further includes a sampling verification module, configured to:

perform sampling verification, where the sampling verification includes: obtaining background light data and mixed light data after the drive current of the light source of the PPG apparatus and the gain of the AFE are adjusted based on the to-be-adjusted current/gain value, and recalculating the actual effective light data based on the obtained background light data and mixed light data.

If the recalculated actual effective light data is beyond the second effective light data range, the light adjustment operation and the sampling verification are cyclically performed.

The embodiments in this specification are described in a progressive manner. For same or similar parts between embodiments, reference may be made to each other. Each embodiment focuses on a difference from other embodiments. For the apparatus embodiments, since they are basically similar to the method embodiments, the description is relatively simple, and reference can be made to the description of the method embodiments.

A person skilled in the art can clearly understand that, for convenience and brevity of description, reference may be made to corresponding processes in the foregoing method embodiments for specific working processes of the foregoing apparatuses and units. Details are not described herein again.

Further, in the 1990s, a technological improvement can be clearly defined as a hardware improvement (for example, an improvement of a circuit structure such as a diode, a transistor, or a switch) or a software improvement (for example, an improvement of a method procedure). However, with development of technologies, improvements of many method procedures can be regarded as direct improvements of hardware circuit structures. Almost all designers obtain a corresponding hardware circuit structure by programming an improved method procedure into a hardware circuit. Therefore, it should not indicate in any way that an improvement of a method procedure cannot be realized by using a hardware entity module, such as a programmable logic apparatus (PLD). In addition, instead of making integrated circuit chips by hand, this kind of programming is also mostly implemented by using logic compiler software, which is similar to a software compiler used in program development and writing. Original code before compiling must also be written in a specific programming language, which is called a hardware description language (HDL). It should be understood by a person skilled in the art that a hardware circuit of a logic method procedure can be easily obtained by using the HDL to perform logic programming on the method procedure and programming the method procedure into an integrated circuit.

In the description of the embodiments of this specification, for ease of description, when the apparatus is described, the functions are divided into various modules and described respectively, and division to the modules is merely division in terms of logical functions. The functions of the modules/units are implemented in the same or a plurality of software and/or hardware.

Specifically, the apparatus proposed in the embodiments of the present disclosure may be fully or partially integrated into a physical entity or may be physically separate. These modules may be all implemented in a form of software through processing element calling; may be all implemented in a form of hardware; or may be partially implemented in a form of software through processing element calling, and partially implemented in a form of hardware. For example, a detection module may be a separate processing element or integrated into a chip of an electronic apparatus. Implementation of other modules is similar. In addition, all or part of these modules may be integrated or implemented independently. During the implementation, each step or module of the foregoing methods may be implemented by an integrated logic circuit of hardware in a processing element or by using an instruction in a form of software.

For example, the foregoing modules may be one or more integrated circuits configured to implement the foregoing methods, such as one or more application-specific integrated circuits (ASICs), one or more digital signal processors (DSPs), or one or more field-programmable gate arrays (FPGAs). For another example, these modules may be integrated and implemented in a form of a system-on-a-chip (SOC).

Those of ordinary skill in the art may be aware that units and algorithm steps described in the embodiments of this specification can be implemented by electronic hardware or a combination of computer software and electronic hardware. Whether these functions are implemented in hardware or software depends on specific applications of the technical solutions and design constraints. A person skilled in the art may use different methods to implement the described functions for each specific application, but such implementation should not be considered to be beyond the scope of this specification.

An embodiment of this specification further provides a PPG apparatus. The PPG apparatus includes a memory configured to store a computer program instruction and a processor configured to execute the computer program instruction. When the computer program instruction is executed by the processor, the electronic apparatus is triggered to perform steps of the methods described in the embodiments of this specification.

Specifically, in an embodiment of this specification, one or more computer programs are stored in the memory, and the one or more computer programs include instructions. When the instructions are executed by the apparatus, the apparatus performs steps of the methods described in the embodiments of this specification.

This specification may be described in general contexts of computer-executable instructions executed by a computer, such as a program module. Generally, the program module includes a routine, a program, an object, a component, a data structure, and the like that perform specific tasks or implement specific abstract data types. This specification may alternatively be practiced in a distributed computing environment in which a task is performed by a remote processing apparatus connected through a communication network. In the distributed computing environment, the program module may be located in local and remote computer storage media including a storage apparatus.

Specifically, in an embodiment of this specification, the processor and the memory may be integrated into a processing apparatus. More generally, the processor and the memory are independent components. The processor is configured to execute the program code stored in the memory to implement the methods described in the embodiments of this specification. During specific implementation, the memory may alternatively be integrated into the processor or independent of the processor.

Further, the apparatus, apparatus, and modules described in the embodiments of this specification may be specifically implemented by a computer chip or entity, or implemented by a product with a specific function.

Persons skilled in the art should understand that the embodiments of this specification may be provided as a method, an apparatus, or a computer program product. Therefore, the present disclosure may use a form of hardware only embodiments, software only embodiments, or embodiments with a combination of software and hardware. Moreover, the present disclosure may be in a form of a computer program product that is implemented on one or more computer-usable storage media that include computer-usable program code.

In the embodiments provided in this specification, if being implemented in a form of a software functional unit and sold or used as a stand-alone product, any function may be stored in a computer-readable storage medium. Based on such an understanding, the technical solutions of this specification essentially, or the part contributing to the prior art, or some of the technical solutions may be implemented in a form of a software product. The computer software product is stored in a storage medium, and includes instructions for instructing a computer apparatus (which may be a personal computer, a server, a network apparatus, or the like) to perform all or some of the steps of the methods described in the embodiments of this specification.

Specifically, an embodiment of this specification provides a computer-readable storage medium. The computer-readable storage medium stores a computer program. When the computer program runs on a computer, the computer executes the methods provided in the embodiments of this specification.

An embodiment of this specification provides a computer program product. The computer program product includes a computer program. When the computer program runs on a computer, the computer executes the methods provided in the embodiments of this specification.

The embodiments of this specification are described with reference to the flowcharts and/or block diagrams of the methods, the apparatus (devices), and the computer program product according to the embodiments of this specification. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of another programmable data processing apparatus to generate a machine, such that the instructions executed by a computer or a processor of another programmable data processing apparatus generate an apparatus for implementing a specific function in one or more processes in the flowcharts and/or in one or more blocks in the block diagrams.

These computer program instructions may be stored in a computer-readable memory that can instruct the computer or any other programmable data processing apparatus to work in a specific manner, such that the instructions stored in the computer-readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing apparatus, such that a series of operations and steps are performed on the computer or the another programmable apparatus, thereby generating computer-implemented processing. Therefore, the instructions executed on the computer or the another programmable apparatus provide steps for implementing a specific function in one or more processes in the flowcharts and/or in one or more blocks in the block diagrams.

It should be noted that in the embodiments of this specification, the term "at least one" refers to one or more, and the term "a plurality of" refers to two or more. The term "and/or" describes associations between associated objects, and indicates three types of relationships. For example, "A and/or B" may indicate that A exists alone, A and B coexist, or B exists alone. "A" and "B" each may be singular or plural. The character "/" generally indicates that the associated objects are in an "or" relationship. The term "at least one of the following" or a similar expression refers to any combination of these items, including any combination of single items or plural items. For example, at least one of a, b, or c may represent: a, b, c, a and b, a and c, b and c, or a and b and c, where a, b, and c may be singular or plural.

In the embodiments of this specification, terms "include", "comprise", or any other variations thereof are intended to cover non-exclusive inclusion, such that a process, method, product, or apparatus including a series of elements not only includes those elements, but also includes other elements that are not explicitly listed, or also includes inherent elements of the process, method, product, or apparatus. Without more restrictions, an element defined by the phrase "including . . . " does not exclude the presence of another same element in a process, method, product, or apparatus that includes the element.

The foregoing merely describes specific implementations of this specification. Any person skilled in the art can easily conceive modifications or replacements within the technical scope of this specification, and these modifications or replacements shall fall within the protection scope of this specification. The protection scope of this specification should be subject to the protection scope of the claims.

What is claimed is:

1. A signal adjustment method for a pshotoplethysmographic (PPG) apparatus, comprising:
   sampling background light data and mixed light data;
   determining whether the background light data falls within a preset background light data range, and/or determining whether calculated actual effective light data falls within a preset first effective light data range, wherein the actual effective light data is a difference between the mixed light data and the background light data; and
   in response to the background light data being beyond the preset background light data range, or the actual effective light data being beyond the preset first effective light data range, performing a light adjustment operation, wherein the light adjustment operation comprises:
      determining an estimated current transfer ratio (CTR) based on a preset CTR or an actual CTR of the PPG apparatus;
      estimating a drive current required by a light source of the PPG apparatus and a gain required by an analog front end (AFE) based on a drive current of the light source, a gain of the AFE, and the sampled background light data and mixed light data;
      calculating estimated effective light data of the PPG apparatus based on the estimated drive current required by the light source, the estimated gain required by the AFE, and the estimated CTR; and
      determining whether the estimated effective light data falls within a preset second effective light data range; and in response to the estimated effective light data falling within the preset second effective light data range, generating a to-be-adjusted current/gain value based on the estimated drive current required by the light source and gain required by the AFE, so as to adjust the drive current of the light source of the PPG apparatus and the gain of the AFE.

2. The method according to claim 1, further comprising: in response to the estimated effective light data being beyond the preset second effective light data range, re-estimating, through convergence, the drive current required by the light source and the gain required by the AFE based on the currently estimated drive current required by the light source and gain required by the AFE, so as to recalculate the estimated effective light data; and in response to the recalculated estimated effective light data falling within the preset second effective light data range, generating a to-be-adjusted current/gain value based on the re-estimated drive current required by the light source and gain required by the AFE.

3. The method according to claim 2, further comprising: in response to the recalculated estimated effective light data being beyond the preset second effective light data range, and the currently estimated drive current and gain falling within a preset adjustable current range and adjustable gain range of the PPG apparatus respectively, re-estimating, through convergence, the drive current required by the light source and the gain required by the AFE.

4. The method according to claim 2, further comprising: in response to the recalculated estimated effective light data being beyond the preset second effective light data range, and the currently estimated drive current and gain being beyond a preset adjustable current range and adjustable gain range respectively, ending the light adjustment operation.

5. The method according to claim 1, wherein the light adjustment operation further comprises: before the drive current required by the light source and the gain required by the AFE are estimated, triggering initial adjustment in response to the background light data being beyond the preset background light data range, wherein the initial adjustment comprises:

adjusting, through convergence, the gain of the AFE.

6. The method according to claim 5, wherein said adjusting, through convergence, the gain of the AFE comprises:
in response to the background light data being greater than an upper limit of the preset background light data range, reducing the gain of the AFE; and
in response to the background light data being less than a lower limit of the preset background light data range, increasing the gain of the AFE.

7. The method according to claim 1, wherein the drive current required by the light source and the gain required by the AFE are estimated through dichotomization or stepping.

8. The method according to claim 1, further comprising: during the drive current required by the light source and the gain required by the AFE being estimated,
in response to the drive current of the light source falling within the preset adjustable current range of the PPG apparatus, adjusting the drive current of the light source; and
in response to the drive current of the light source being beyond the preset adjustable current range of the PPG apparatus, and the gain of the AFE falling within the preset adjustable gain range of the PPG apparatus, adjusting the gain of the AFE.

9. The method according to claim 1, wherein said determining an estimated CTR based on an actual CTR of a PPG apparatus comprises:

calculating the actual CTR when the PPG apparatus samples the mixed light data based on a drive current of the light source and a gain of the AFE when the mixed light data is sampled, and the calculated actual effective light data, wherein the estimated CTR is an actual CTR when the mixed light data is sampled for one time, or an average value of a plurality of actual CTRs when the mixed light data is sampled for a plurality of times.

10. The method according to claim 1, wherein said determining whether the background light data falls within a preset background light data range comprises:
in response to background light data sampled for an $n^{th}$ time or for each time of n consecutive times being beyond the preset background light data range, determining that the background light data is beyond the preset background light data range.

11. The method according to claim 1, wherein said determining whether calculated actual effective light data falls within a preset first effective light data range comprises:
in response to effective light data calculated for an $n^{th}$ time or for each time of n consecutive times being beyond the preset first effective light data range, determining that the effective light data is beyond the preset first effective light data range.

12. The method according to claim 1, wherein in response to a light leakage level threshold falling within the preset first effective light data range, defining that a lower limit of the second effective light data range is the light leakage level threshold, wherein the light leakage level threshold is a parameter value determined based on a light leakage status of the PPG apparatus in an application scenario.

13. The method according to claim 1, wherein said generating a to-be-adjusted current/gain value based on the estimated drive current required by the light source and gain required by the AFE in response to the estimated effective light data falling within the preset second effective light data range comprises:
obtaining an apparatus jitter parameter of the PPG apparatus;
calling or calculating a corresponding attenuation coefficient based on the apparatus jitter parameter; and
performing attenuation calculation on the estimated drive current required by the light source and gain required by the AFE based on the attenuation coefficient, and using a result of the attenuation calculation as the to-be-adjusted current/gain value.

14. The method according to claim 1, further comprising:
performing sampling verification, wherein the sampling verification comprises:
after the drive current of the light source of the PPG apparatus and the gain of the AFE are adjusted based on the to-be-adjusted current/gain value, obtaining background light data and mixed light data; and recalculating the actual effective light data based on the obtained background light data and mixed light data; and
in response to the recalculated actual effective light data being beyond the second effective light data range, cyclically performing the light adjustment operation and the sampling verification.

15. A pshotoplethysmographic (PPG) apparatus, comprising a memory configured to store a computer program instruction and a processor configured to execute the computer program instruction, wherein when the computer program instruction is executed by the processor, the PPG apparatus is triggered to perform steps of a signal adjustment method, which comprises:

sampling background light data and mixed light data;

determining whether the background light data falls within a preset background light data range, and/or determining whether calculated actual effective light data falls within a preset first effective light data range, wherein the actual effective light data is a difference between the mixed light data and the background light data; and in response to the background light data being beyond the preset background light data range, or the actual effective light data being beyond the preset first effective light data range, performing a light adjustment operation, wherein the light adjustment operation comprises:

determining an estimated current transfer ratio (CTR) based on a preset CTR or an actual CTR of the PPG apparatus;

estimating a drive current required by a light source of the PPG apparatus and a gain required by an analog front end (AFE) based on a drive current of the light source, a gain of the AFE, and the sampled background light data and mixed light data;

calculating estimated effective light data of the PPG apparatus based on the estimated drive current required by the light source, the estimated gain required by the AFE, and the estimated CTR; and determining whether the estimated effective light data falls within a preset second effective light data range; and in response to the estimated effective light data falling within the preset second effective light data range, generating a to-be-adjusted current/gain value based on the estimated drive current required by the light source and gain required by the AFE, so as to adjust the drive current of the light source of the PPG apparatus and the gain of the AFE.

16. The PPG apparatus according to claim 15, further comprising: in response to the estimated effective light data being beyond the preset second effective light data range, re-estimating, through convergence, the drive current required by the light source and the gain required by the AFE based on the currently estimated drive current required by the light source and gain required by the AFE, so as to recalculate the estimated effective light data; and in response to the recalculated estimated effective light data falling within the preset second effective light data range, generating a to-be-adjusted current/gain value based on the re-estimated drive current required by the light source and gain required by the AFE.

17. The PPG apparatus according to claim 16, further comprising: in response to the recalculated estimated effective light data being beyond the preset second effective light data range, and the currently estimated drive current and gain falling within a preset adjustable current range and adjustable gain range of the PPG apparatus respectively, re-estimating, through convergence, the drive current required by the light source and the gain required by the AFE; and in response to the recalculated estimated effective light data being beyond the preset second effective light data range, and the currently estimated drive current and gain being beyond a preset adjustable current range and adjustable gain range respectively, ending the light adjustment operation.

18. A computer-readable storage medium, wherein the computer-readable storage medium stores a computer program, and when the computer program runs on a pshotoplethysmographic (PPG) apparatus, the PPG apparatus performs steps of a signal adjustment method, which comprises:

sampling background light data and mixed light data;

determining whether the background light data falls within a preset background light data range, and/or determining whether calculated actual effective light data falls within a preset first effective light data range, wherein the actual effective light data is a difference between the mixed light data and the background light data; and in response to the background light data being beyond the preset background light data range, or the actual effective light data being beyond the preset first effective light data range, performing a light adjustment operation, wherein the light adjustment operation comprises:

determining an estimated current transfer ratio (CTR) based on a preset CTR or an actual CTR of the PPG apparatus;

estimating a drive current required by a light source of the PPG apparatus and a gain required by an analog front end (AFE) based on a drive current of the light source, a gain of the AFE, and the sampled background light data and mixed light data;

calculating estimated effective light data of the PPG apparatus based on the estimated drive current required by the light source, the estimated gain required by the AFE, and the estimated CTR; and determining whether the estimated effective light data falls within a preset second effective light data range; and in response to the estimated effective light data falling within the preset second effective light data range, generating a to-be-adjusted current/gain value based on the estimated drive current required by the light source and gain required by the AFE, so as to adjust the drive current of the light source of the PPG apparatus and the gain of the AFE.

19. The computer-readable storage medium according to claim 18, further comprising: in response to the estimated effective light data being beyond the preset second effective light data range, re-estimating, through convergence, the drive current required by the light source and the gain required by the AFE based on the currently estimated drive current required by the light source and gain required by the AFE, so as to recalculate the estimated effective light data; and in response to the recalculated estimated effective light data falling within the preset second effective light data range, generating a to-be-adjusted current/gain value based on the re-estimated drive current required by the light source and gain required by the AFE.

20. The computer-readable storage medium according to claim 19, further comprising: in response to the recalculated estimated effective light data being beyond the preset second effective light data range, and the currently estimated drive current and gain falling within a preset adjustable current range and adjustable gain range of the PPG apparatus respectively, re-estimating, through convergence, the drive current required by the light source and the gain required by the AFE; and in response to the recalculated estimated effective light data being beyond the preset second effective light data range, and the currently estimated drive current and gain being beyond a preset adjustable current range and adjustable gain range respectively, ending the light adjustment operation.

\* \* \* \* \*